United States Patent
Wanunu et al.

(10) Patent No.: US 11,703,476 B2
(45) Date of Patent: Jul. 18, 2023

(54) METHOD AND APPARATUS FOR SENSING A MOLECULE

(71) Applicant: Northeastern University, Boston, MA (US)

(72) Inventors: Meni Wanunu, Needham, MA (US); Mohammadamin Alibakhshi, Boston, MA (US); Xinqi Kang, Boston, MA (US); Zhuoyu Zhang, Brooklyn, NY (US)

(73) Assignee: NORTHEASTERN UNIVERSITY, Boston, MA (US)

( * ) Notice: Subject to any disclaimer, the term of this patent is extended or adjusted under 35 U.S.C. 154(b) by 401 days.

(21) Appl. No.: 17/083,264

(22) Filed: Oct. 28, 2020

(65) Prior Publication Data

US 2021/0123884 A1 Apr. 29, 2021

Related U.S. Application Data

(60) Provisional application No. 62/927,063, filed on Oct. 28, 2019.

(51) Int. Cl.
*G01N 27/416* (2006.01)
*B01L 3/00* (2006.01)
*G01N 33/487* (2006.01)

(52) U.S. Cl.
CPC ...... *G01N 27/4166* (2013.01); *B01L 3/50273* (2013.01); *B01L 3/502707* (2013.01);
(Continued)

(58) Field of Classification Search
CPC .......... G01N 27/4166; G01N 33/48721; B01L 3/502707; B01L 3/502715; B01L 3/50273;
(Continued)

(56) References Cited

U.S. PATENT DOCUMENTS 6,863,833 B1 * 3/2005 Bloom .................. B81B 1/004
436/71
8,137,569 B2 3/2012 Harnack et al.
(Continued)

FOREIGN PATENT DOCUMENTS

EP 3598133 A1 1/2020
EP 3776080 A 2/2021
(Continued)

OTHER PUBLICATIONS

Afonin, K. A, et al., "In Vitro Assembly of Cubic RNA-Based Scaffolds Designed in Silico," Nat. Nanotechnol. 2010, 5, 676-682.
(Continued)

*Primary Examiner* — Dennis White
(74) *Attorney, Agent, or Firm* — Hamilton, Brook, Smith & Reynolds, P.C.

(57) ABSTRACT

An apparatus is provided for sensing a molecule in a sample. The apparatus utilizes an electric field to draw molecules from a first chamber through an aperture, defined by a chemical layer, into a second chamber. The apparatus can detect a DNA molecule with, for example, 4, 5, or 6 unique base pairs. As molecules pass through the aperture, a sensor detects or measures a change in an electric parameter used to generate the electric field, thereafter translating the change in the electric parameter into information about the molecule. A divider element separates the first and second chambers and supports a chemical layer defining the aperture. The apparatus enables detection or measurement of molecules over prolonged time at a higher electric field strength than other nanopores, due to a combination of the shape of the divider, structural elements thereon, and thickness of the chemical layer at the aperture.

13 Claims, 30 Drawing Sheets
(19 of 30 Drawing Sheet(s) Filed in Color)

(52) U.S. Cl.
CPC .. *B01L 3/502715* (2013.01); *G01N 33/48721* (2013.01); *B01L 2300/0645* (2013.01); *B01L 2300/0832* (2013.01); *B01L 2400/0406* (2013.01); *B01L 2400/0415* (2013.01)

(58) Field of Classification Search
CPC ..... B01L 2300/0645; B01L 2300/0832; B01L 2400/0406; B01L 2400/0415
See application file for complete search history.

(56) References Cited

U.S. PATENT DOCUMENTS

| | | | |
|---|---|---|---|
| 8,513,165 | B2 | 8/2013 | Takeuchi et al. |
| 8,663,780 | B2 | 3/2014 | Harnack et al. |
| 11,073,764 | B2 | 7/2021 | Wanunu et al. |
| 11,313,857 | B2 | 4/2022 | Wanunu et al. |
| 2003/0169618 | A1 | 9/2003 | Lindsey et al. |
| 2007/0238679 | A1 | 10/2007 | Rank et al. |
| 2009/0214622 | A1 | 8/2009 | Poinern et al. |
| 2011/0263129 | A1 | 10/2011 | Shin et al. |
| 2013/0294972 | A1 | 11/2013 | Kinz-Thompson et al. |
| 2014/0329225 | A1 | 11/2014 | Morin |
| 2015/0090588 | A1 | 4/2015 | Shepard et al. |
| 2016/0062239 | A1 | 3/2016 | Morgan et al. |
| 2016/0200773 | A1 | 7/2016 | Morin |
| 2017/0363741 | A1 | 12/2017 | Send et al. |
| 2018/0043310 | A1 | 2/2018 | Bustamante et al. |
| 2018/0045668 | A1 | 2/2018 | Hyun et al. |
| 2019/0305619 | A1 | 10/2019 | Wanunu |
| 2019/0310245 | A1 | 10/2019 | Wanunu |
| 2020/0363406 | A1 | 11/2020 | Chen et al. |
| 2021/0405533 | A1 | 12/2021 | Wanunu et al. |
| 2022/0334097 | A1 | 10/2022 | Wanunu et al. |
| 2023/0017101 | A1 | 1/2023 | Alibakhshi et al. |

FOREIGN PATENT DOCUMENTS

| | | |
|---|---|---|
| GB | 1337626 A | 11/1973 |
| WO | WO 2016/133570 A1 | 8/2016 |
| WO | WO 2016/161402 A1 | 10/2016 |
| WO | WO 2019/191490 A1 | 10/2019 |
| WO | WO 2021/062306 A1 | 4/2021 |

OTHER PUBLICATIONS

Afonin, K. A, et al., "Specific RNA Self-Assembly with Minimal Paranemic Motifs," J. Am. Chem. Soc. 2008, 130, 93-102.
Afonin, K. A, et al., "Design and Self-Assembly of SiRNA-Functionalized RNA Nanoparticles for Use in Automated Nanomedicine," Nat. Protoc. 2011, 6, 2022-2034.
Afonin, K. A, et al., "Computational and Experimental Characterization of RNA Cubic Nanoscaffolds," Methods 2014, 67, 256-265.
Afonin, K. A, et al.. "In Silico Design and Enzymatic Synthesis of Functional RNA Nanoparticles," Acc. Chem. Res. 2014, 47, 1731-1741.
Afonin, K. A, et al., "Engineered RNA Nanodesigns for Applications in RNA Nanotechnology." DNA RNA Nanotechnol. 2013, 1 1-15.
Afonin, K. A, et al., "Multifunctional RNA Nanoparticles," Nano Lett. 2014, 14, 5662-5671.
Akahori et al., "Discrimination of Three Types of Homopolymers in Single-stranded DNA with Solid-state Nanopores through External Control of the DNA Motion," Sci. Rep. 2017, 7, 9073.
Akeson et al., "Microsecond Time-Scale Discrimination Among Polycytidylic Acid, Polyadenylic Acid, and Polyuridylic Acid as Homopolymers or as Segments Within Single RNA Molecules," Biophys. J. 1999, 77, 3227-3233.
Aksimentiev et al., "Microscopic Kinetics of DNA Translocation through Synthetic Nanopores," Biophys. J. 2004, 87, 2086-2097.
An, N., et al., J. Proc Natl Acad Sci USA 2014, 111, (40), 14325-31.
Andersen, H. C., et al., "Rattle: A "Velocity" Version of the Shake Algorithm for Molecular Dynanlics Calculations," J. Comput. Phys. 1983, 52, 24-34.
Andersen, E. S., et al., "Self-Assembly of a Nanoscale DNA Box with a Controllable Lid," Nature 2009, 459, 73-76.
Auernheimer et al., "Photoswitched cell adhesion on surfaces with RGD peptides," J. Am. Chem. Soc. 127, 16107-16110 (2005).
Azagarsamy et al., "Wavelength-controlled photocleavage for the orthogonal and sequential release of multiple proteins," Angew. Chem. Int. Ed. EngL 52, 13803-13807 (2013).
Bacri, L., et al., "Discrimination of Neutral Oligosaccharides through a Nanopore," Biochem. Biophys. Res. Commun. 2011, 412, 561-564.
Batcho et al., "Optimized Particle-Mesh Ewald/Multiple-Time Step Integration for Molecular Dynamics Simulations," J. Chem. Phys. 2001, 115, 4003-4018.
Bavley, H., "Nanopore Sequencing: From Imagination to Reality," Clin. Chem. 2015, 61, 25-31.
Bell et al., "Asymmetric Dynamics of DNA Entering and Exiting a Strongly Confining Nanopore," Nat. Commun. 2017, 8, 380.
Best et al., "Optimization of the Additive CHARMM All-Atom Protein Force Field Targeting Improved Sampling of the Backbone φ, ψ, and Side-Chain X1 and X2 Dihedral Angles," J. Chem. Theory Comput. 2012, 8, 3257-3273.
Bhagawati, M., et al., "Native laser lithography of His-tagged proteins by uncaging of multivalent chelators," J. Am. Chem. Soc. 132, 5932-5933 (2010).
Bhatia, D., el al., "Icosahedral DNA Nanocapsules by Modular Assembly," Angew. Chem., Int. Ed. 2009, 48, 4134-4137.
Bhatia. D., et al., "Quantum Dot-Loaded Monofunctionalized DNA Icosahedra for Single-Particle Tracking of Endocytic Pathways," Nat. Nanotechnol. 2016, 11, 1112-1119.
Bluemmel, J., et al., "Protein repellent properties of covalently attached PEG coatings on nanostructured SiO(2)-based interfaces," Biomaterials 28, 4739-4747 (2007).
Boekhoven, J., et al., "Dynamic display of bioactivity through host-guest chemistry," Angew. Chem. Int. Ed. EngL 52, 12077-12080 (2013).
Branton, D., et al., "The Potential and Challenges of Nanopore Sequencing," Nat. Biotechnol. 2008, 26, 1146-1153.
Brieke, C., et al., "Lightcontrolled tools," Angew. Chem. Int. Ed. EngL 51, 8446-8476 (2012).
Bui, et al., "Versatile RNA Tetra-U Helix Linking Motif as a Toolkit for Nucleic Acid Nanotechnology," Nanomedicine 2017, 13, 1137-1146.
Bujold, K E., et al., "Optimized DNA "Nanu Suitcases" for Encapsulation aml Cumlitiunal Release of SiRNA," J. Am. Chem. Soc. 2016, 138, 14030-14038.
Cai et al., "Resistive-Pulse Measurements with Nanopipettes: Detection of Vascular Endothelial Growth Factor C (Vegf-C) Using Antibody-Decorated Nanoparticles," Anal. Chem. 2015, 87, 6403-6410.
Carson et al., "Smooth DNA Transport through a Narrowed Pore Geometry," Biophys. J. 2014, 107, 2381-2393.
Carson, S., et al., "Challenges in DNA Motion Control and Sequence Readout Using Nanopore Devices," Nanotechnology 2015, 26, 074004.
Cassinelli, V., et al., "One-Step Formation of "Chain-Armor" -Stabilized DNA Nanostructures," Angew. Chem., Int. Ed. 2015, 54, 7795-7798.
Chidchob, P., et al., "Synergy of Two Assembly Languages in DNA Nanostructures: Self-Assembly of Sequence-Defined Polymers on DNA Cages," J. Am. Chem. Soc. 2016, 138, 4416-4425.
Comer et al., "Microscopic Mechanics of Hairpin DNA Translocation through Synthetic Nanopores," Biophys. J. 2009, 96, 593-608.
Cruz-Chu et al., "Water-Silica Force Field for Simulating Nanodevices," J. Phys. Chem. B 2006, 110, 21497-21508.
Cui el al., "Light-triggered multifunctionality at surfaces mediated by photolabile protecting groups," Macromol. Rapid Commun. 34, 310-329 (2013).
Daedalus, "DNA Origami Sequence Design Algorithm for User-defined Structures," 2018, 2 pages.

(56) References Cited

OTHER PUBLICATIONS

Darden et al., "Particle Mesh Ewald: An N• Log (N) Method for Ewald Sums in Large Systems," J. Chem. Phys. 1993, 98, 10089-10092.
Dao, et al., "Triggering RNAi with Multifunctional RNA Nanoparticles and Their Delivery," DNA RNA Nanotechnol. 2015, 1, 27-38.
Dekker, C., "Solid-State Nanopores," Nat. Nanotechnol. 2007, 2, 209-215.
Deshpande et al. "Optical Properties of Silicon Nitride Films Deposited by Hot Filament Chemical Vapor Deposition," J. Appl. Phys. 1995, 77, 6534-6541.
Dibrov, el al., "Self -Assembling RNA Square," Proc. Natl. Acad. Sci. U.S.A. 2011, 108, 6405-6408.
Fennouri, A, et al., "Single Molecule Detection of Glycosaminoglycan Hyaluronic Acid Oligosaccharides and Depolymerization Enzyme Activity Using a Protein Nanopore," ACS Nano 2012, 6, 9672-9678.
Fologea et al., "DNA Conformation and Base Number Simultaneously Determined in a Nanopore," Electrophoresis 2007, 28, 3186-3192.
Fologea, D., et al., "Electrical Characterization of Protein Molecules by a Solid-State Nanopore," Appl. Phys. Lett. 2007, 91, 053901.
Fournier et al., "The Solubility of Amorphous Silica at High Temperatures and High Pressures," Am. Mineral. 1977, 62, 1052-1056.
Firnkes, M., et al., "Electrically Facilitated Translocations of Proteins through Silicon Nitride Nanopores: Conjoint and Competitive Action of Diffusion, Electrophoresis and Electroosmosis," Nano Lett. 2010, 10, 2162-2167.
Gershow et al., "Recapturing and Trapping Single Molecules with a Solid-State Nanopore," Nat. Nanotechnol. 2007, 2, 775-779.
Gilboa et al., "Optically-Monitored Nanopore Fabrication Using a Focused Laser Beam", Sci. Rep. 2018, 8, 9765.
Giorgis et al., "Optical Absorption and Photoluminescence Properties of a-Sil-xNx: H Films Deposited by Plasma-enhanced CVD," Phys. Rev. B: Condens. Matter Mater. Phys. 2000, 61, 4693-4698.
Graf et al., "Fabrication and practical applications of molybdenum disulfide nanopores," Nature Protocols, Nature Publishing Group, GB, vol. 14, No. 4, Mar. 22, 2019, pp. 1130-1168.
Goodman, R.P., et al., "Rapid Chiral Assembly of Rigid DNA Building Blocks for Molecular Nanofabrication," Science 2005, 310, 1661-1665.
Grabow, et al., "Self-Assembling RNA Nanorings Based on RNAi/Ii Inverse Kissing Complexes," Nano Lett., 2011 11 878-887.
Gropeanu, M., et al., "A versatile toolbox for multiplexed protein micropatterning by laser lithography,". Small 9, 838-845 (2013).
Grunwald, C., et al., "From the Cover: In situ assembly of macromolecular complexes triggered by light," Proc. Natl Acad. Sci. USA 107, 6146-6151 (2010).
Guo, P., et al., "Construction of Folate-Conjugated pRNA of Bacteriophage Phi29 DNA Packaging Motor for Delivery of Chimeric SiRNA to Nasopharyngeal Carcinoma Cells." Gene Ther. 2006, 13, 1553.
Guo, S., et al., "Specific Delivery of Therapeutic RNAs to Cancer Cells Via the Dimerization Mechanism of Phi29 Motor pRNA," Hum. Gene Ther. 2005, 16, 1097-1109.
Guo, P., "The Emerging Field of RNA Nanotechnology," Nat. Nanotechnol. 2010, S, 833-842.
Guo, P., et al., "Uniqueness, Advantages, Challenges, Solutions, and Perspectives in Therapeutics Applying RNA Nanotechnology," Nucleic Acid Ther. 2012, 22, 226-245.
Guo, P., et al., "Inter-RNA Interaction of Phage phi29 pRNA to Form a Hexameric Complex for Viral DNA Transportation," Mol. Cell 1998, 2, 149-155.
Halman, J. R, et al., "Functionally-Interdependent Shape-Switching Nanoparticles with Controllable Properties," Nucleic Acids Res. 2017, 45, 2210-2220.
Han, D., et al., "Single-molecule spectroelectrochemical cross-correlation during redox cycling in recessed dual ring electrode zero-mode waveguides," Chemical science 2017, 8 (8), 5345-5355.
Han, D., et al., "Redox cycling in nanopore-confined recessed dual-ring electrode arrays," The Journal of Physical Chemistry C 2016, 120 (37), 20634-20641.
Haque, F., et al., "Solid-State and Biological Nanopore for Real-Time Sensing of Single Chemical and Sequencing of DNA," Nano Today 2013, 8, 56-74.
He Y, et al., "Hierarchical Self-Assembly of DNA into Symmetric Supramolecular Polyhedra," Nature 2008, 452, 198-202.
Heng, et al., "Stretching DNA Using the Electric Field in a Synthetic Nanopore," Nano Lett. 2005, 5, 1883-1888.
Henley, "Osmium-Based Pyrimidine Contrast Tags for Enhanced Nanopore-Based DNA Base Discrimiation," PlosONE 2015, 12 pages (2015).
Hofmeister et al., "Patterned polymer matrix promotes sternness and cell-cell interaction of adult stem cells", Journal of Biological Engineering, Biomed Central Ltd, vol. 9, article 18, Oct. 12, 2015 Oct. 12, 2015), pp. 1-9.
Holden et al., "Electrical Signature of the Deformation and Dehydration of Microgels During Translocation through Nanopores," Soft Matter 2011, 7, 8035-8040.
Holden et al., "Resistive Pulse Analysis of Microgel Deformation During Nanopore Translocation," J. Phys. Chem. C 2011, 115, 2999-3004.
Howorka, et al., "Nanopore Analytics: Sensing of Single Molecules," Chem. Soc. Rev. 2009, 38, 2360-2384.
Hu, "Differential Enzyme Flexibility Probed Using Solid-State Nanopores," ACS Nano 2018, 12: 4494-4502 (2018).
Huang et al., "Large-Area Synthesis of Highly Crystalline WSe2 Monolayers and Device Applications," ACS Nano, vol. 8, No. 1, Jan. 28, 2014, pp. 923-930.
Ivankin, "Labeled-Free Optical Detection of Biomolecular Translocation Through Nanopore Arrays," ACS Nano 2014, 8: 10774-10781 (2014).
Jadhav, V.; et al., "Porous Zero-Mode Waveguides for Picogram-Level DNA Capture," Nano letters 2018, 19 (2), 921-929.
Kaneko, S., et al., "Photocontrol of cell adhesion on amino-bearing surfaces by reversible conjugation of poly(ethylene glycol) via a photocleavable linker," Phys. Chem. Chem. Phys. 13, 4051-4059 (2011).
Kasianowicz, et al., "Nanoscopic Porous Sensors," Amw. Rev. Anal. Chem. 2008, 1, 737-766.
Keyser et al., "Nanopore Tomography of a Laser Focus," Nano Lett. 2005, 5, 2253-2256.
Kim, M. J., et al., "Characteristics of Solid-State Nanometre Pores Fabricated Using a Transmission Electron Microscope," Nanotechnology 2007, 18, 205302.
Kim, J., et al., "Mimicking dynamic in vivo environments with stimuli-responsive materials for cell culture." Trends Biotechnol. 30, 426-439 (2012).
Kim et al., "Generation of SiRNA Nanosheets for Efficient RNA Interference," Sci. Rep. 2016, 6, 25146.
Kim, M. J., et al., "Rapid Fabrication of Uniformly Sized Nanopores and Nanopore Arrays for Parallel DNA Analysis," Adv. Mater. 2006, 18, 3149-3153.
Klan, P., el al., "Photoremovable protecting groups in chemistry and biology: reaction mechanisms and efficacy," Chem. Rev. 113, 119-191 (2013).
Kloxin., et al., "Photodegradable hydrogels for dynamic tuning of physical and chemical properties," Science 324, 59-63 (2009).
Kloxin., et al., "Tunable hydrogels for external manipulation of cellular microenvironments through controlled photodegradation," Adv. Mater. 22, 61-66 (2010).
Korlach, J, el al., "Selective aluminum passivation for targeted immobilization of single DNA polymerase molecules in zero-mode waveguide nanostructures," Proc Natl Acad Sci U S A 2008, 105 (4), 1176-1181.
Kowalczyk et al., "Modeling the Conductance and DNA Blockade of Solid-state Nanopores," Nanotechnology 2011, 22, 315101.

(56) References Cited

OTHER PUBLICATIONS

Laboria, N., et al., "Control of nanomolar interaction and in situ assembly of proteins in four dimensions by light," Angew. Chem. Int. Ed. EngL 52, 848-853 (2013).
Lamb et al., "Redox-switchable surface for controlling peptide structure," J. Am. Chem. Soc. 133, 8870-8873 (2011).
Larkin, J.; et al., "High-Bandwidth Protein Analysis Using Solid-State Nanopores," Biophys. J. 2014, 106, 696-704.
Larkin, J.; et al., "Reversible positioning of single molecules inside zero-mode waveguides," Nano letters 2014, 14 (10), 6023-6029.
Larkin, J.; et al., "Length-independent DNA packing into nanopore zero-mode waveguides for low-input DNA sequencing," Nature nanotechnology 2017, 12 (12), 1169.
Lee et al., "A Low-Noise Solid-State Nanopore Platform Based on a Highly Insulating Substrate," Sci. Rep. 2015, 4, 7448.
Lee et al., "Light-triggered in vivo activation of adhesive peptides regulates cell adhesion, inflammation and vascularization of biomaterials," Nat. Mater. 14, 352-360 (2015).
Li, H., et al., "Controllable Self-Assembly of RNA Tetrahedrons with Precise Shape and Size for Cancer Targeting," Adv. Mater. 2016, 28, 7501-7507.
Li, J., et al., "Characterization of Protein Unfolding with Solid-State Nanopores," Protein Pept. Lett. 2014, 21, 256-265.
Li, J., et al., "The Distribution of DNA Translocation Tinies in Solid-State Nanopores," J. Phys.: Condens. Matter 2010, 22, 454129.
Lin et al., "Characterization of DNA duplex Unzipping through a Sub-2 nm Solid-state Nanopore," Chem. Commun. 2017, 53, 3539-3542.
Liu et al., "Atomically Thin Molybdenum Disulfide Nanopores with High Sensitivity for DNA Translocation," ACS Nano, vol. 8, No. 3, Feb. 18, 2014, pp. 2504-2511.
Liu, B., et al., "Dynamic presentation of immobilized ligands regulated through biomolecular recognition," J. Am. Chem. Soc. 132, 13630-13632 (2010).
Liu, Z., et al., "Self-Assembly of Responsive Multilayered DNA Nanocages," J. Am. Chem. Soc. 2015, 137, 1730-1733.
Liu, D., et al., "Using azobenzene-embedded self-assembled monolayers to photochemically control cell adhesion reversibly." Angew. Chem. Int. Ed. Engl. 48, 4406-4408 (2009).
Lombardo et al., "Dielectric Breakdown Mechanisms in Gate Oxides," J. Appl. Phys. 2005, 98, 121301.
Martin, W. E., et al., "A comparison of single-molecule emission in aluminum and gold zero-mode waveguides," The Journal of Physical Chemistry A 2016, 120 (34), 6719-6727.
Martyna et al., "Constant Pressure Molecular Dynamics Algorithms," J. Chem. Phys. 1994, 101, 4177-4189.
Matsuda., et al., "Tissue engineering based on cell sheet technology," Adv. Mat. 19, 3089-3099 (2007).
McPherson et al., "Underlying Physics of the Thermochemical E Model in Describing Low-field Time-dependent Dielectric Breakdown in SiO2 Thin Films." J. Appl. Phys. 1998, 84, 1513-1523.
Meller et al., "Rapid Nanopore Discrimination between Single Polynucleotide Molecules." Proc. Natl. Acad. Sci. U.S.A. 2000, 97, 1079-1084.
MicroPlex Non-Magnetic Microspheres, "Coupled to Protein or Nucleic Acid," 12 pages.
Miyamoto et al.., "An Analytical Version of the Shake and Rattle Algorithm for Rigid Water Models," J. Comput. Chem. 1992, 13, 952-962.
Nakanishi, J., et al., "Photoactivation of a substrate for cell adhesion under standard fluorescence microscopes," J. Am. Chem. Soc. 126, 16314-16315 (2004).
Nazari, et al., "Femtosecond Photonic Viral Inactivation Probed Using Solid-State Nanopores," Cornell University Library, Jun. 5, 2018.
Ng, C.C.A., et al., "Using an electrical potential to reversibly switch surfaces between two states for dynamically controlling cell adhesion," Angew. Chem. Int. Ed. Engl. 51, 7706-7710 (2012).
Nicoli et al., "DNA Translocations through Solid-State Plasmonic Nanopores," Nano Lett. 2014, 14, 6917-6925.
Ohmuro-Matsuyama, Y., et al., Photocontrolled cell adhesion on a surface functionalized with a caged arginine-glycine-aspartate peptide. Angew. Chem. Int. Ed. Engl. 47, 7527-7529 (2008).
Ohno, H., et al., "Synthetic RNA Protein Complex Shaped Like an Equilateral Triangle," Nat. Nanotechnol. 2011, 6, 116-120.
Osada, E., et al., "Engineering RNA-Protein Complexes with Different Shapes for Imaging and Therapeutic Applications," ACS Nano 2014, 81 8130-8140.
Pant et al., "Etching of Silicon Nitride in CC12F2, CHF3, SiF4. and SF6 Reactive Plasma: A Comparative Study," Plasma Chem. Plasma Process. 1999, 19, 545-563.
Petersen et al., Phototriggering of cell adhesion by caged cyclic RGD peptides. Angew. Chem. Int. Ed. Engl. 47, 3192-3195 (2008).
Pevarnik, M., et al., "Particle Deformation and Concentration Polarization in Electroosmotic Transport of Hydrogels through Pores," ACS Nano 2013, 7, 3720-3728.
Phillips et al., "Scalable Molecular Dynamics with NAMD," J. Comput. Chem. 2005, 26, 1781-1802.
Plesa, C., et al., "Ionic Permeability and Mechanical Properties of DNA Origami Nanoplates on Solid-State Nanopores," ACS Nano 2014, 8, 35-43.
Pud et al: "Self-Aligned Plasmonic Nanopores by Optically Controlled Dielectric Breakdown", Nano Letters, vol. 15, No. 10, Oct. 14, 2015 (Oct. 14, 2015), pp. 7112-7117.
Reineke et al., "Shift of pH-Value During Thermal Treatments in Buffer Solutions and Selected Foods," Int. J. Food Prop. 2011, 14, 870-881.
Reiner, J. E., et al., "Disease Detection and Management Via Single Nanopore-Based Sensors," Chem. Rev. 2012, 112, 6431-6451.
Robertus, J., et al., "Dynamic control over cell adhesive properties using molecular-based surface engineering strategies," Chem. Soc. Rev. 39, 354-378 (2010).
Rolli et al., "Switchable adhesive substrates: revealing geometry dependence in collective cell behavior," Biomaterials 33, 2409-2418 (2012).
Rosenstein, J., et al., "Integrated Nanopore Sensing Platform with Sub-Microsecond Temporal Resolution," Nat. Methods 2012, 9, 487-492.
Rothemund et al., "Dielectric Breakdown of Reactively Sputtered Silicon Nitride," Thin Solid Films 1973, 15, 199-205.
Rudenko et al., "Planar electro-optofluidic chip: Integration of nanopore with optofluidics", Conference on Lasers and Electro-Optics (CLEO) and Quantum Electronics and Laser Science Conference (QELS), May 16-21, 2010, pp. 1-2.
Saleh et al., "Direct Detection of Antibody-Antigen Binding Using an on-Chip Artificial Pore," Proc. Natl. Acad. Sci. U.S.A., 2003, 100, 820-824.
Saliemo et al., "Photo-activatable surfaces for cell migration assays," Advan. Funct. Mater. 23, 5974-5980 (2013).
Schenk, F. C., et al., "Dual-fimctionalized nanostructured biointerfaces by click chemistry," Langmuir 30, 6897-6905 (2014).
Shlyakhtenko et al., "Silatrane-Based Surface Chemistry for Immobilization of DNA, Protein-DNA Complexes and Other Biological Materials," Ultramicroscopy 2003, 97, 279-287.
Squires, A, et al., "Chapter Fourteen-Single-Molecule Characterization of DNA-Protein Interactions Using Nanopore Biosensors," Methods Enzymol. 2017, 582, 353-385.
Staffa et al., "Temperature Dependence of the Etch Rate and Selectivity of Silicon Nitride over Silicon Dioxide in Remote Plasma NF3/C12," Appl. Phys. Lett. 1995, 67, 1902-1904.
Stewart et al., "Programmable RNA Microstractures for Coordinated Delivery of SiRNAs," Nanoscale 2016, 8, 17542-17550.
Talaga, et al.,., "Single-Molecule Protein Unfolding in Solid-State Nanopores," J. Am. Chem. Soc. 2009, 131, 9287-9297.
van Beest et al., "Force Fields for Silicas and Aluminophosphatcs Based on ab initio Calculations," Phys. Rev. Lett., 1990, 64, 1955-1958.
Venkatesan, B. M., et al., "Nanopore Sensors for Nucleic Acid Analysis," Nat. Nanotechnol. 2011, 6, 615-624.
Venta et al., "Differentiation of Short, Single-Stranded DNA Homopolymers in Solid-State Nanopores," ACS Nano 2013, 7, 4629-4636.

(56) References Cited

OTHER PUBLICATIONS

Waduge, et al., "Direct and Scalable Deposition of Atomically Thin Low-Noise MoS2 Membranes on Apertures," ACS Nano, vol. 9, No. 7, Jan. 1, 2015, pp. 7352-7359.

Waduge, et al., "Nanopore-Based Measurements of Protein Size, Fluctuations, and Conformational Changes," ACS Nano 2017, 11, 5706-5716.

Wang, S., et al., "Engineered Nanopore of Phi29 DNA-Packaging Motor for Real-Time Detection of Single Colon Cancer Specific Antibody in Serum," ACS Nano 2013, 7, 9814-9822.

Wang, Y., et al., "Resistive-Pulse Measurements with Nanopipettes: Detection of Au Nanoparticles and Nanoparticle-Bound Anti-Peanut Igy," Chem. Sci. 2013, 4, 655-663.

Wanunu, M., "Nanopores: A Journey Towards DNA Sequencing," Phys. Life Rev. 2012, 9, 125-158.

Wanunu, M., et al., "DNA Translocation Governed by Interactions with Solid-State Nanopores," Biophys. J. 2008, 95, 4716-4725.

Wanunu, M., et al., "Nanopore Analysis of Individual RNA/Antibiotic Complexes," ACS Nano 2011, 5, 9345-9353.

Wanunu et al., "Rapid Electronic Detection of Probe-specific microRNAs using Thin Nanopore Sensors," Nat. Nanotechnol. 2010, 5, 807-814.

Wegner et al., "Photocleavable linker for the patterning of bioactive molecules," Scientific Reports 5, Article No. 18309 (2015).

Weis et al., "Dynamic cell-adhesive microenvironments and their effect on myogenic differentiation," Acta Biomaterialia 9, 8059-8066 (2013).

Wirkner et al., "Photoactivatable caged cyclic RGD peptide for triggering integrin binding and cell adhesion to surfaces," Chembiochem 12, 2623-2629 (2011).

Wirkner et al., "Triggered cell release from materials using bioadhesive photocleavable linkers." Adv. Mat. 23, 3907-3910 (2011).

Wu et al., "The Estimation of Field-Dependent Conductance Change of Nanopore by Field-Induced Charge in the Translocations of Aunps-DNA Conjugates," J. Phys. Chem. C 2014, 118, 26825-26835.

Yamazaki et al., "Label-Free Single-Molecule Thermoscopy Using a Laser-Heated Nanopore," Nano Lett. 2017, 17, 7067-7074.

Yamazaki et al., "Photothermally Assisted Thinning of Silicon Nitride Membranes for Ultrathin Asymmetric Nanopores", ACS Nano, 2018, 12, pp. 12472-12481.

Yeo et al., "Dynamic interfaces between cells and surfaces: electroactive substrates that sequentially release and attach cells," J. Am. Chem. Soc. 125, 14994-14995 (2003).

Turkan Yigitbasi (2012). Multiplex Immunoassay and Bead Based Multiplex, Trends in Immunolabelled and Related Techniques, Dr. Eltayb Abuelzein (Ed.). ISBN: 978-953-51-0570-1, InTech, Available from: http://www.intechopen.com/books/trends-in-immunolabelled-and-related-techniques/bead-based-multiplex.

Ying et al., "Formation of Single Nanopores with Diameters of 20-50 nm in Silicon Nitride Membranes Using Laser-Assisted Controlled Breakdown," ACS Nano, 2019, vol. 12, pp. 11458-11470.

Ying et al., "3D Nanopore Shape Control by Current-Stimulus Dielectric Breakdown", Applied Physics Letter 109, 063105. (Year: 2016).

Yingling et al., "Computational Design of an RNA Hexagonal Nanoring and an RNA Nanotube," Nano Lett., 2007, 7, 2328-2334.

Yoo et al., "Competitive Binding of Cations to Duplex DNA Revealed through Molecular Dynamics Simulations," J. Phys. Chem. B 2012, 116, 12946-12954.

Yu, J., et al., "De Novo Design of an RNA Tile That Self-Assembles into a Homo-Octameric Nanoprism," Nat. Commun. 2015, 6, 5724.

Zhang, Z., et al., "Programmable hydrogels for controlled cell catch and release using hybridized aptamers and complementary sequences," J. Am. Chem. Soc. 134, 15716-15719 (2012).

Alibakhshi, M. A., et al., "Picomolar Fingerprinting of Nucleic Acid Nanoparticles Using Solid-State Nanopores," ACS Nano, 11(10): 9701-9710 (2017).

Baker, C. A., et al., "Photolithographic Fabrication of Microapertures with Well-Defined, Three-Dimensional Geometries for Suspended Lipid Membrane Studies," Anal. Chem., 85: 9078-9086 (2013).

Burden, D. L. et al., "Mechanically Enhancing Planar Lipid Bilayers with a Minimal Actin Cortex," Langmuir, 34: 10847-10855 (2018).

Cao, C.; et al., "Mapping the sensing spots of aerolysin for single oligonucleotides analysis," Nature Communications, 9(2823): 1-9 (2018).

Clarke, J., et al., "Continuous base identification for single-molecule nanopore DNA sequencing," Nature Nanotechnology, 4: 265-270 (2009).

Derrington, I. M., et al., "Nanopore DNA sequencing with MspA," Proc. Natl. Acad. Sci. USA, 107(37): 16060-16065 (2010).

Ding, Y., et al., "Internal vs Fishhook Hairpin DNA: Unzipping Locations and Mechanisms in the α-Hemolysin Nanopore," J. Phys. Chem. B, 118: 12873-12882 (2014).

Fahie, M., et al., "Resolved Single-Molecule Detection of Individual Species within a Mixture of anti-Biotin Antibodies Using an Engineered Monomeric Nanopore," ASC Nano, 9(2): 1089-1098 (2015).

Fleming, A. M., et al., "Oxidative DNA damage is epigenetic by regulating gene transcription via base excision repair," Proc. Natl. Acad. Sci. USA, 114(10): 2604-2609 (2017).

Fuller, C. W., et al., "Real-time single-molecule electronic DNA sequencing by synthesis using polymer-tagged nucleotides on a nanopore array," Proc. Natl. Acad. Sci. USA, 113(19): 5233-5238 (2016).

Gopfrich, K., et al., "Large-Conductance Transmembrane Porin Made from DNA Origami," ACS Nano, 10: 8207-8214 (2016).

Harrington, L., et al., "Pim Kinase Inhibitors Evaluated with a Single-Molecule Engineered Nanopore Sensor," Angew. Chem., 127: 8272-8277 (2015).

Harrington, L., et al., "Single-Molecule Protein Phosphorylation and Dephosphorylation by Nanopore Enzymology," ACS Nano, 13: 633-641 (2018).

Henrickson, S. E., et al., "Driven DNA Transport into an Asymmetric Nanometer-Scale Pore," J. Physical Review Letters, 85(14): 3057-3060 (2000).

Hernandez-Ainsa, S. and Keyser, U.F., "DNA origami nanopores: developments, challenges and perspectives," Royal Soc. Chem. Nanoscale, pp. 1-12 (2014).

Hirano-Iwata, A., et al., Free-Standing Lipid Bilayers in Silicon Chips-Membrane Stabilization "Based on Microfabricated Apertures with a Nanometer-Scale Smoothness," Langmuir, 26(3): 1949-1952 (2010).

Huang, G., et al., "FraC nanopores with adjustable diameter identify the mass of opposite-charge peptides with 44 dalton resolution," Nature Communications, 10(835): 1-10 (2019).

Jeon, T. J., et al., "Hydrogel-Encapsulated Lipid Membranes," J. Am. Chem. Soc., 128: 42-43 (2006).

Jeon, T. J., et al., "Black, lipid membranes stabilized through substrate conjugation to a Hydrogel," J. Biointerphases, 3(2): FA96-FA100 (2008).

Ji, Z., et al., "Nano-channel of Viral DNA Packaging Motor as Single Pore to Differentiate Peptides with Single Amino Acid Difference," Biomaterials, 182: 227-233 (2018). (From Biomaterials, Author Manuscript, available in PMC, pp. 1-14 (2019)).

Jin, Q., et al., "Unzipping Kinetics of Duplex DNA Containing Oxidized Lesions in an α-Hemolysin Nanopore," J. Am. Chem. Soc., 134: 11006-11011 (2012).

Kalsi, S., et al., "Shaped Apertures in Photoresist Films Enhance the Lifetime and Mechanical Stability of Suspended Lipid Bilayers," Biophysical J., 106(8): 1650-1659 (2014).

Kang, X. F., et al., "A Storable Encapsulated Bilayer Chip Containing a Single Protein Nanopore," J. Am. Chem. Soc., 129: 4701-4705 (2007).

Kowal, J., et al., "Hybrid Polymer-Lipid Films as Platforms for Directed Membrane Protein Insertion," Langmuir, 31: 4868-4877 (2015).

Kumar, M., et al., "High-Density Reconstitution of Functional Water Channels into Vesicular and Planar Block Copolymer Membranes," J. Am. Chem. Soc., 134: 18631-18637 (2012).

(56) References Cited

OTHER PUBLICATIONS

Langecker, M., et.al., "Nanopores Suggest a Negligible Influence of CpG Methylation on Nucleosome Packaging and Stability," *Nano Lett.*, 15: 783-790 (2015).

Liu, B., et al., "Bilayer lipid membrane (BLM) based ion selective electrodes at the meso-, micro-, and nano-scales," *Biosensors and Bioelectronics*, 24: 1843-1849 (2009).

Maglia, G., et al., "Enhanced translocation of single DNA molecules through α-hemolysin nanopores by manipulation of internal charge," *Proc. Natl. Acad. Sci. USA*, 105(50): 19720-19725 (2008).

Maglia, G., et al., "Analysis of single nucleic acid molecules with protein Nanopores," *Methods Enzymol*, 475, 591-623 (2010). (From Author Manuscript available in PMC, pp. 1-30, (2011)).

Malmstadt, N., et al., "Long-Lived Planar Lipid Bilayer Membranes Anchored to an In Situ Polymerized Hydrogel," *J. Adv. Mater.*, 20: 84-89 (2008).

Mathe, J., et al., "Nanopore Unzipping of Individual DNA Hairpin Molecules," *Biophys. J.*, 87(5): 3205-3212 (2004).

Mathé, J., et al., "Orientation discrimination of single-stranded DNA inside the α-hemolysin membrane channel," *Proc. Natl. Acad. Sci. USA*, 102(35): 12377-12382 (2005).

Mayer, M., et al., "Microfabricated Teflon Membranes for Low-Noise Recordings of Ion Channels in Planar Lipid Bilayers," *Biophys. J.*, 85(4): 2684-26895 (2003).

Meller, A. and Branton, D., "Single molecule measurements of DNA transport through a nanopore," *Electrophoresis*, 23: 2583-2591 (2002).

Morton, D., et al., "Tailored polymeric membranes for *Mycobacterium smegmatis* porin A (MspA) based Biosensors," *J. Mater. Chem. B*, 3: 5080-5086 (2015).

Nakane, J., et al., "Evaluation of nanopores as candidates for electronic analyte detection," *Electrophoresis*, 23: 2592-2601 (2002).

Nardin, C., et al., "Giant Free-Standing ABA Triblock Copolymer Membranes," *Langmuir*, 16: 7708-7712 (2000).

Nivala, J., et al., "Unfoldase-mediated protein translocation through an α-hemolysin nanopore," *Nat. Biotechnol.*, 31(3): 247-250 (2013).

Noakes, M. T., et al., "Increasing the accuracy of nanopore DNA sequencing using a time-varying cross membrane voltage," *Nature Biotechnology*, pp. 1-10 (2019).

O'Shaughnessy, T. J., et al., "Laser ablation of micropores for formation of artificial planar lipid bilayers," *Biomed Microdevices*, 9: 863-868 (2007).

Pang, Y.; Shu, Y. et al., "3D Stretchable Arch Ribbon Array Fabricated via Grayscale Lithography," *Scientific Reports*, 6(28552): 1-8 (2016).

Piguet, F. et al., "Identification of single amino acid differences in uniformly charged homopolymeric peptides with aerolysin nanopore," *Nature Communications*, 9: 1-13 (2018).

Rodriguez-Larrea, D. and Bayley, H., "Multistep protein unfolding during nanopore Translocation," *Nature Nanotechnology*, 8, 288-295 (2013).

Rofeh, J., et al., "Microfluidic block copolymer membrane arrays for nanopore DNA sequencing," *Appl. Phys. Lett.*, 114 (213701): 1-6 (2019).

Shasha, C., et al., "Nanopore-Based Conformational Analysis of a Viral RNA Drug Target," *Acs Nano*, 8: A-F (2014).

Shim, J. W. and Gu, L. Q., "Stochastic Sensing on a Modular Chip Containing a Single-Ion Channel," *Anal. Chem.*, 79: 2207-13 (2007).

Studer, A., et al., "Integration and recording of a reconstituted voltage-gated sodium channel in planar lipid bilayers," *Biosensors and Bioelectronics*, , 26: 1924-1928 (2011).

Tadaki, D., et al., "Mechanically stable solvent free lipid bilayers in nano- and micro-tapered apertures for reconstitution of cell-free synthesized hERG channels," *Sci. Rep.*, 7(17736): 1-10 (2017).

Thakur, A. K. and Movileanu, L., "Real-time measurement of protein-protein interactions at single-molecule resolution using a biological nanopore," *Nature Biotechnology*, 37(1): 96-104 (2018).

Vercoutere, W., et al., "Rapid discrimination among individual DNA hairpin molecules at single-nucleotide resolution using an ion channel," *Nature Biotechnology*, 19: 248-252 (2001).

Wang, Y., et al., "Nanopore-based detection of circulating microRNAs in lung cancer patients," *Nature Nanotechnology*, 6: 668-674 (2011).

Wanunu, M., et al., "Electrostatic focusing of unlabelled DNA into nanoscale pores using a salt gradient" *Nature Nanotechnology*, 5: 160-165 (2010).

Wescoe, Z. L., et al., "Nanopores Discriminate Among Five C5-Cytosine Variants in DNA," *J. Am. Chem. Soc.*, pp. 1-14 (2014).

White, R. J., et al., White, H. S., "Single Ion-Channel Recordings Using Glass Nanopore Membranes," *J. Am. Chem. Soc.*, 129: 11766-11775 (2007).

Wong, D. and Jeon, T.-J.; Schmidt, J., "Single molecule measurements of channel proteins incorporated into biomimetic polymer membranes," *Nanotechnology*, 17: 3710-3717 (2006).

Zakharian, E., "Recording of Ion Channel Activity in Planar Lipid Bilayer Experiments," *Methods Mol. Biol.*, 998(8): 109-118 (2013).

Zhou, S., et al., "Label-free nanopore single-molecule measurement of trypsin activity," *ACS Sensors*, pp. 1-30 (2016).

\* cited by examiner

FIG. 12

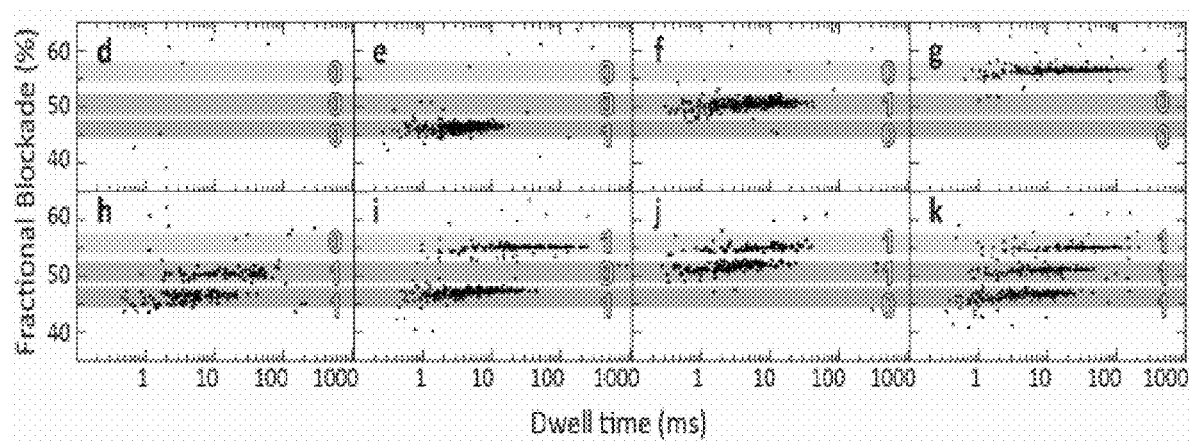
FIGs. 17D-K

METHOD AND APPARATUS FOR SENSING A MOLECULE

RELATED APPLICATION

This application claims the benefit of U.S. Provisional Application No. 62/927,063 filed on Oct. 28, 2019. The entire teachings of the above application are incorporated herein by reference.

GOVERNMENT SUPPORT

This invention was made with government support under Grant No. 1645671 from the National Science Foundation. The government has certain rights in the invention.

BACKGROUND

Nanopores are versatile, low-cost, and label-free biosensors that have been used for a variety of applications, including DNA sequencing; biophysical studies; sensing RNA, peptides, and proteins; studying DNA-protein and protein-protein interactions; and measuring enzyme activity. Biological nanopores are channels composed of either proteins or DNA origami structures that self-assemble and insert into a lipid bilayer or polymer membrane. Compared with their solid-state counterparts, biological nanopores are more structurally reproducible, easier to produce at large scales, and have already shown great potential for DNA sequencing and biosensing applications.

SUMMARY OF THE INVENTION

Typically, pore chemistry and geometry must be adapted to sense each class of analytes. For example, short nucleic acids, such as microRNAs (miRNAs), translocate a pore at a timescale that requires very high bandwidths to measure, while on the other hand, proteins are typically too large and only can traverse the pores in their fully denatured form. Therefore, developing a method for reliable release and detection of reporter hairpins is essential in developing this general biosensing modality.

In order to pass molecules through biological nanopores, they are usually inserted into a lipid bilayer membrane that separates two chambers filled with an electrolyte solution. Applying a voltage bias across the pore results in a steady-state ion current with a flux that is limited by the pore constriction, such that a highly localized electric field is produced. When a biomolecule is captured by the electric field, the current flux is partially blocked by the presence of the biomolecule, resulting in a current blockade that corresponds to the molecule's size, charge, and conformation.

In order to develop a universal sensing strategy that is suitable for detecting a wide range of target molecules in nanopores (e.g., nucleic acids, protein biomarkers, metabolites, drugs, and biomolecular complexes), one approach is to sense the target analyte indirectly by sensing a surrogate molecule that reports the presence and concentration of a certain target analyte in the sample. The reporter molecules must be detectable with the nanopores in a multiplexed fashion, i.e., to produce distinct signature ionic current signals while traversing a pore. It has been shown that individual DNA hairpins that differ only by a single base pair in their stem length can be discriminated in α-hemolysin nanopores based on signals they produce during their accommodation in the pore vestibule. Useful to this resolution and efficient detection of short hairpins is their long-lived residence times in the pore, which is orders of magnitude faster than the passage times of single-stranded DNA molecules of similar lengths through the α-hemolysin pore constriction. Therefore, the DNA hairpins are prime candidates to serve as reporter molecules in a universal sensing method.

In a typical assay, reporter hairpins are conjugated to target molecules already immobilized onto a surface of microbeads through various mechanisms that include Watson-Crick base pairing for nucleic acid target molecules or sandwich enzyme-linked immunosorbent assays (ELISAs) for protein targets, and release of these hairpins followed by their detection using a nanopore to identify the presence and concentration of the target analyte.

Following that general description of embodiments of the invention, below are some particular example embodiments.

In an embodiment, an apparatus for sensing a molecule comprises a housing defining a volume, a divider element in the housing that defines a first chamber and a second chamber within the volume, multiple structural elements extending from a surface of the divider, a chemical layer coupled to the divider element on opposing surfaces of the divider element, a first electrode within the first chamber, a second electrode within the second chamber, and a sensor.

The divider element defines a gap for fluidic communication between the first and second chambers. The divider element decreases in thickness from a distal location to a proximal location relative to the gap. The first and the second chambers are capable of containing a sample with molecules therein. The multiple structural elements extend from a surface of the divider element and are located between the distal location and proximal location within the second chamber. Adjacent structural elements are separated by a respective distance. The chemical layer forms an aperture in the gap of sufficient dimensions for a given molecule to pass therethrough. The first and second electrodes, disposed within the first and the second chambers, respectively, compose an electrode pair. When energized, the electrode pair generates an electric field at a level sufficient to cause the molecules to pass from the first chamber via the aperture to the second chamber. The sensor is configured to sense the molecule as it passes through the aperture.

In some embodiments, the multiple structural elements have a geometric shape with size varying from the distal location to the proximal location. The adjacent structural elements may also vary in respective distance from the distal location to the proximal location. In some embodiments, the structural elements are cylindrical pillars. In some embodiments, the adjacent structural elements have respective distances that facilitate a capillary action of a fluid at the proximal location relative to the distal location among the multiple structural elements.

In some embodiments, the multiple structural elements have a height extending from a surface of the divider element approximately to a common plane offset from the surface of the divider element. In some embodiments, the gap is substantially circular and has a diameter from about 50 μm to about 250 μm. In some embodiments, the aperture has a dimension that may facilitate the passage of the molecule therethrough in a manner that denatures the molecule. In some embodiments, the chemical layer may withstand a voltage differential from about 100 mV to about 400 mV at the aperture for up to eight hours. In some embodiments, the sensor has a sensitivity to detect or measure a voltage or current change provided to the first electrode or the second electrode during passage of the molecule through the aperture.

In some embodiments, the sensor is electronic and has a sensitivity that enables the sensor to detect or measure a change in voltage or current provided to the first electrode or the second electrode during the passage of a hairpin molecule through the aperture. In some embodiments, the sensor has sufficient sensitivity to discriminate between different hairpin molecules, the hairpin molecules having different a distinguishing feature. In some embodiments, the distinguishing feature includes a number of base pairs or a sequence mismatch. In some embodiments, a power source is electrically coupled to the first electrode and the second electrode.

In an embodiment, a method for manufacturing an apparatus for sensing a molecule comprises forming a component for an apparatus for sensing a molecule, forming structural elements, and producing a film of chemical layer. The component defines a portion thereof that decreases in thickness between a first surface of the component and a second surface of the component from a distal location to a proximal location relative to a gap defined through the component. The gap extends between the first surface and the second surface. In one embodiment, producing the film of chemical layer includes adhering the chemical layer to the first surface of the component and to the second surface of the component at least proximal to the gap. In some embodiments, the component is exposed to a light, the light having an intensity that increases from a central location of an aperture to an edge location of the aperture, which, using grayscale photolithography, causes the component to have a wedge shape of decreasing thickness, as described above.

In an embodiment, a method for sensing a molecule in a sample comprises retaining a fluid at a chemical layer in a second chamber, energizing an electrode pair, and sensing a molecule. The fluid at the chemical layer in the second chamber is retained therein by capillary action induced by multiple structural elements defined on a surface of a divider element. The chemical layer defines an aperture that senses a passing of a molecule from a first chamber to a second chamber. The electrode pair includes a first electrode disposed within the first chamber defined by a housing and divider element disposed therein and a second electrode disposed within the second chamber within the housing of an opposing surface of the divider element from the first chamber. The electrode pair generates an electric field that passes through the aperture defined by the chemical layer. The electric field has a strength of sufficient magnitude to cause a molecule in a sample in the first chamber to pass from the first chamber via the aperture to the second chamber, thereby sensing the molecule as it passes through the aperture.

In some embodiments, sensing the molecule includes detecting or measuring a change in an electrical parameter associated with generating the electric field as the molecule passes through the aperture. In some embodiments, a strength of the electric field at the aperture in combination with a dimension of the aperture causes the molecule to be denatured as it passes through the aperture. In some embodiments, sensing the molecule is performed with sufficient sensitivity to discriminate between or among different hairpin compounds passing through the aperture. In some embodiments, an organic matter is coupled to the chemical layer at the aperture, wherein sensing the molecule senses the molecule as it passes from the first chamber to the second chamber through a channel defined by the organic matter.

In an embodiment, a system for sensing a molecule in a sample comprises an apparatus, a power source, and a sensor. The apparatus has a housing, a divider element defining a first chamber and a second chamber within the housing and defining a gap through the divider element. The divider element has a thickness decreasing from a distal location to a proximal location of the gap. The divider element defines multiple structural elements on a surface of the divider element. The multiple structural elements are configured to induce a capillary action. The apparatus further has a chemical layer forming a film in the gap and an aperture within the film. The housing includes an electrode pair that includes a first electrode in the first chamber and a second electrode in a second chamber. The power source is electrically coupled to the electrode pair that, when energized, causes a molecule to pass from the first chamber via the aperture to the second chamber. The sensor is configured to detect or measure a change of an electrical signal, used to produce the electric field, as the molecule passes from the first chamber through the aperture to the second chamber.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 4C-2 is a scatter plot of fractional current blockade versus dwell time obtained from analysis of a four-minute recording of a hairpin mixture cut from the beads using a negative control in which hairpins were exposed to BglII, in accordance with an embodiment of the invention.

FIG. 4C-3 is a scatter plot of fractional current blockade versus dwell time obtained from analysis of a four-minute recording of a hairpin mixture cut from the beads using a negative control in which no DNA hairpin was immobilized on beads, in accordance with an embodiment of the invention.

FIG. 12 depicts DNA hairpin sequences and the restriction enzyme's recognition site, in accordance with an embodiment of the invention.

FIGS. 17D-K depict scatter plots of fractional current blockade versus dwell time for all eight combinations of three hairpins in a mixture, in accordance with an embodiment of the invention.

DESCRIPTION OF EXAMPLE EMBODIMENTS

A description of example embodiments follows.

Among the existing single-molecule sensing technologies, nanopores are versatile, low-cost, and label-free biosensors that have been used for a variety of applications, including DNA sequencing, biophysical studies, sensing RNA, peptides, and proteins, studying DNA-protein and protein-protein interactions, and measuring enzyme activity. Biological nanopores are channels composed of either proteins or DNA origami structures that self-assemble and insert into a lipid bilayer or polymer membrane. Compared with their solid-state counterparts, biological nanopores are more structurally reproducible and easier to produce at large scales and have already shown great potential for DNA sequencing and biosensing applications. In order to pass molecules through them, biological nanopores usually insert into a lipid bilayer membrane which separates two chambers filled with an electrolyte solution. Applying a voltage bias across the pore results in a steady-state ion current with a flux that is limited by the pore constriction, such that a highly localized electric field is produced. When a biomolecule is captured by the electric field, the current flux is partially blocked by the presence of the biomolecule, resulting in a current blockade that corresponds to the molecule's size, charge, and conformation.

Figure 1A:
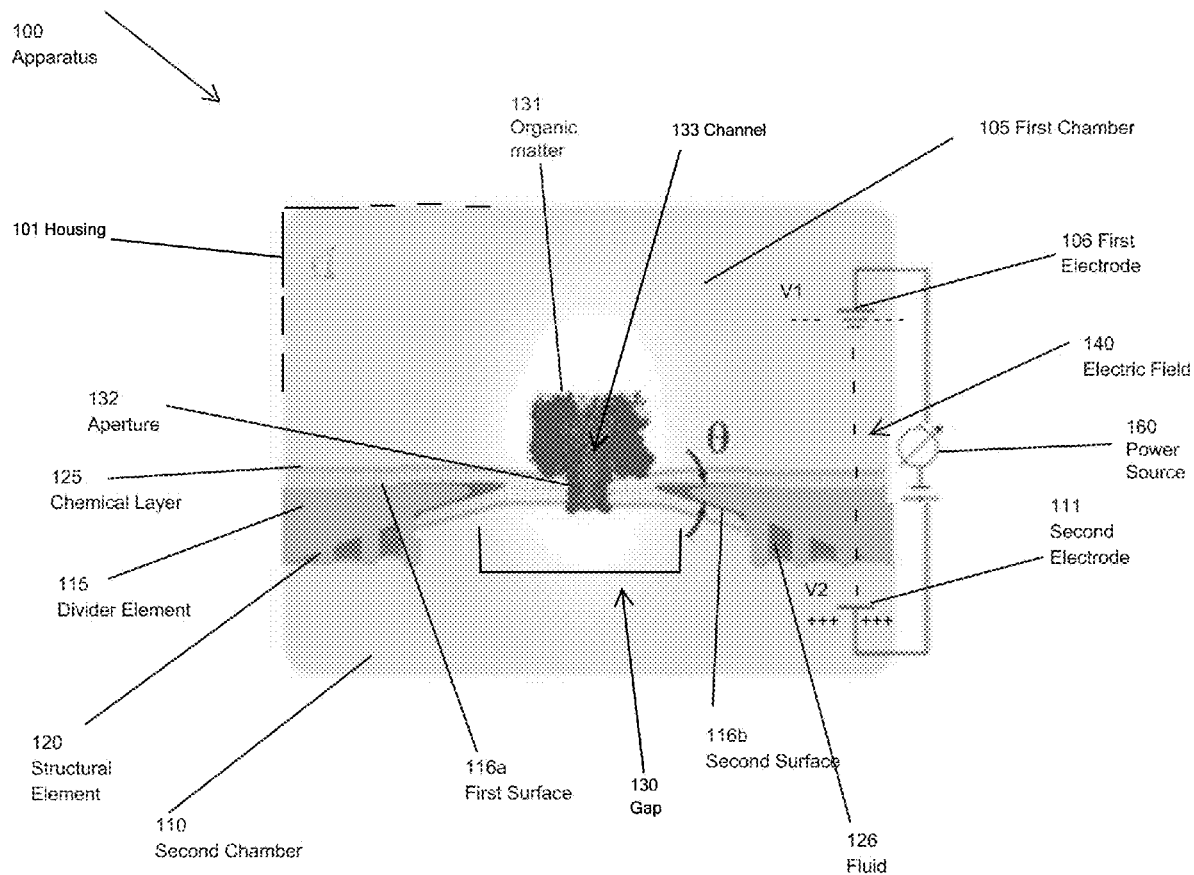
FIG. 1A is a schematic diagram of a molecule sensing apparatus, in accordance with an embodiment of the invention.
Figure 1B:
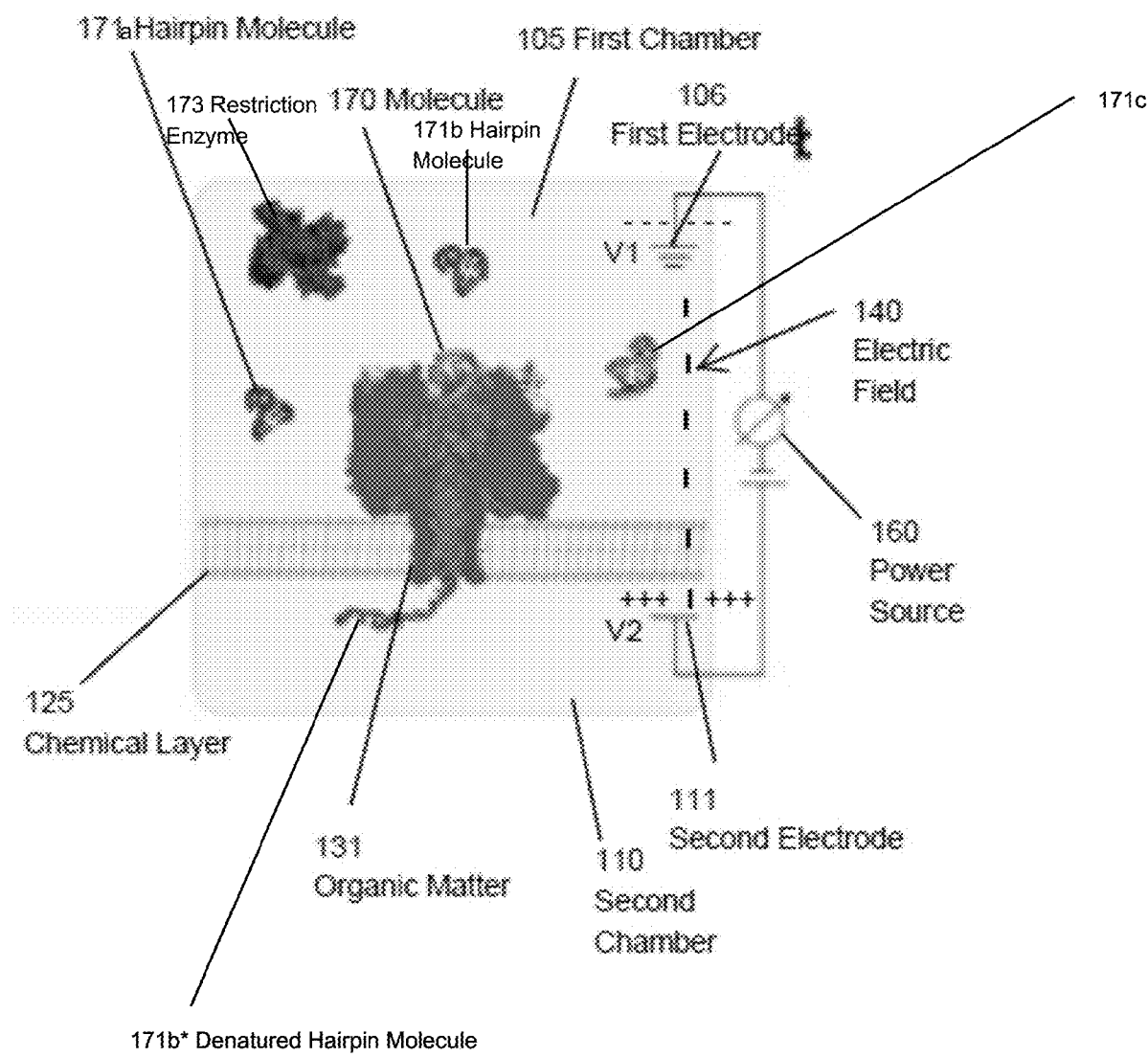
FIG. 1B is a schematic diagram of a molecule sensing apparatus illustrating the presence of a hairpin molecule, in accordance with an embodiment of the invention.
Figure 1C:
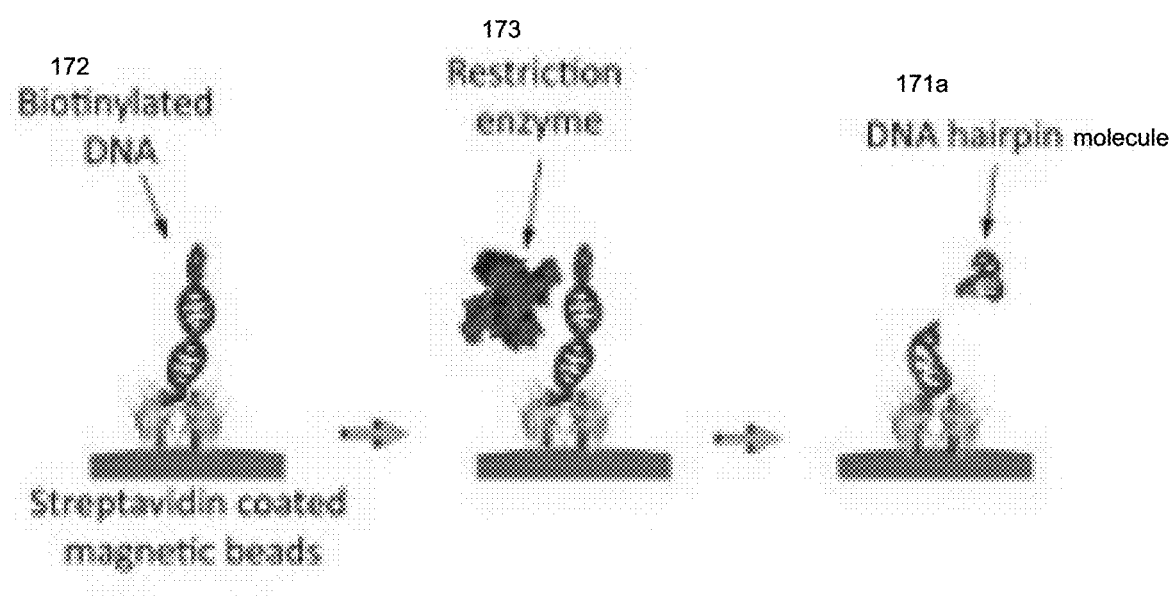
FIG. 1C is a schematic of releasing DNA hairpins using a restriction enzyme and magnetic beads, in accordance with an embodiment of the invention.

In some embodiments, and as seen in FIGS. 1A-C, a system for sensing a molecule 170 in a sample comprises an apparatus 100, a power source 160, and a sensor. The apparatus 100 has a housing, a divider element 115 defining a first chamber 105 and a second chamber 110 within the housing and defining a gap 130 through the divider element 115. The divider element 115 has a thickness decreasing from a distal location to a proximal location of the gap 130.

The divider element 115 defines multiple structural elements 120 on a surface of the divider element 115. The multiple structural elements 120 are configured to induce a capillary action. The apparatus 100 further has a chemical layer 125 forming a film in the gap 130 and an aperture 132 within the film. The housing includes an electrode pair that includes a first electrode 106 in the first chamber 105 and a second electrode 111 in a second chamber 110. The power source 160 is electrically coupled to the electrode pair that, when energized, cause a molecule 170 to pass from the first chamber 105 via the aperture 132 to the second chamber 110. The sensor is configured to detect or measure a change of an electrical signal, used to produce the electric field 140, as the molecule 170 passes from the first chamber 105 through the aperture 132 to the second chamber 110.

FIG. 1A illustrates an apparatus for sensing a molecule. The apparatus 100 for sensing a molecule 170 comprises a housing defining a volume, a divider element 115 in the housing that defines a first chamber 105 and a second chamber 110 within the volume, multiple structural elements 120 extending from a surface of the divider, a chemical layer 125 coupled to the divider element 115 on opposing surfaces of the divider element 115, a first electrode 106 within a first chamber 105, a second within a second chamber 110, and a sensor.

The divider element 115 defines a gap 130 for fluidic communication between the first and second chamber 110. The divider element 115 decreasing in thickness from a distal location to a proximal location relative to the gap 130. The first and the second chamber 110 are capable of containing a sample with the molecule 170 therein. The multiple structural elements 120 extending from a surface of the divider element 115 are located between the distal location and proximal location within the second chamber 110. Adjacent structural elements 120 are separated by a respective distance. The chemical layer 125 forms an aperture 132 in the gap 130 of sufficient dimensions for a given molecule 170 to pass therethrough. The first and second electrodes, disposed within the first and the second chamber 110 respectively, compose an electrode pair. When energized, the electrode pair generates an electric field 140 at a level sufficient to cause the molecule 170 to pass from the first chamber 105 via the aperture 132 to the second chamber 110. The sensor is configured to sense the molecule 170 as it passes through the aperture 132.

In some embodiments, the multiple structural elements 120 have a geometric shape with size varying from the distal location to the proximal location. The adjacent structural elements 120 vary in respective distance from the distal location to the proximal location. In some embodiments, the structural elements 120 are cylindrical pillars. In some embodiments, the adjacent structural elements 120 have respective distances that facilitate a capillary action of a fluid 126 at the proximal location relative to the distal location among the multiple structural elements 120.

While many different classes of molecules and biopolymers have been sensed using nanopores, typically the pore chemistry and geometry must be adapted to sense each class of analytes. For example, short nucleic acids such as microRNAs (miRNAs) translocate the pore at a timescale that requires very high bandwidths to measure, while on the other hand, proteins are typically too large, and only can traverse the pores in their fully denatured form. In order to develop a universal sensing strategy that is suitable for detecting a wide range of target molecules in nanopores (e.g., nucleic acids, protein biomarkers, metabolites, drugs, and biomolecular complexes), one approach is to indirectly sense the target analyte by sensing a surrogate molecule that reports the presence and concentration of a certain target analyte in the sample. The reporter molecules must be detectable with the nanopores in a multiplexed fashion, i.e., to produce distinct signature ionic current signals while traversing a pore.

In some embodiments, and as depicted in FIG. 1A-C, the multiple structural elements 120 have a geometric shape with size varying from the distal location to the proximal location. The adjacent structural element 120$s$ vary in respective distance from the distal location to the proximal location. In some embodiments, the structural element 120$s$ are cylindrical pillars. In some embodiments, the adjacent structural element 120$s$ have respective distances that facilitate a capillary action of a fluid 126 at the proximal location relative to the distal location among the multiple structural elements 120.

In some embodiments, the multiple structural elements 120 have a height extending from a surface of the divider element 115 approximately to a common plane offset from the surface of the divider element 115. In some embodiments, the gap 130 is substantially circular and has a diameter from about 50 µm to about 250 µm. In some embodiments, the aperture 132 has a dimension that may facilitate the passage of the molecule 170 therethrough in a manner that denatures the molecule 170. In some embodiments, the chemical layer 125 may withstand a voltage differential from about 100 mV to about 400 mV at the aperture 132 for up to eight hours. In some embodiments, the sensor has a sensitivity to detect or measure a voltage or current change provided to the first electrode 106 or the second electrode 111 during passage of the molecule 170 through the aperture 132. In some embodiments, the sensor is electronic and has a sensitivity that enables the sensor to detect or measure a change in voltage or current provided to the first electrode 106 or the second electrode 111 during the passage of a hairpin molecule 171 through the aperture 132. In some embodiments, the sensor has sufficient sensitivity to discriminate between different hairpin molecule 171, the hairpin molecule 171 having different a distinguishing feature. In some embodiments, the distinguishing feature includes a number of base pairs or a sequence mismatch. In some embodiments, a power source 160 is electrically coupled to the first electrode 106 and the second electrode.

It has been shown that individual DNA hairpins differing only by a single base pair in their stem length can be discriminated in α-hemolysin nanopores based on signals they produce during their accommodation in the pore vestibule. Important to this resolution and efficient detection of short hairpins is their long-lived residence times in the pore, which is orders of magnitude faster than the passage times of single-stranded DNA molecules of similar lengths through the α-hemolysin pore constriction. Therefore, the DNA hairpins, also referred to herein as hairpin molecules, are prime candidates to serve as reporter molecules in a universal sensing scheme. In a typical assay, reporter hairpins are conjugated to target molecules already immobilized onto the surface of the microbeads through various mechanisms that include Watson-Crick base pairing for nucleic acid target molecules or sandwich ELISA (enzyme-linked immunosorbent assay) for protein targets, and release of these hairpins followed by their detection using a nanopore identifies the presence and concentration of the target analyte. Therefore, developing a method for reliable release and detection of reporter hairpins is essential in developing this general biosensing modality.

In some embodiments, a method for sensing a molecule 170 in a sample comprises retaining a fluid 126 at a chemical layer 125 in a second chamber 110, energizing an electrode pair, and sensing a molecule 170. The fluid 126 at the chemical layer 125 in the second chamber 110 is retained therein by capillary action induced by multiple structural elements 120 defined on a surface of a divider element 115. The chemical layer 125 defines an aperture 132 that senses a passing of a molecule 170 from a first chamber 105 to a second chamber 110. The electrode pair includes a first electrode 106 disposed within the first chamber 105 defined by a housing and divider element 115 disposed therein and a second electrode 111 disposed within the second chamber 110 within the housing of an opposing surface of the divider element 115 from the first chamber 105. The electrode pair generates an electric field 140 that passes through the aperture 132 defined by the chemical layer 125. The electric field 140 has a strength of sufficient magnitude to cause a molecule 170 in a sample in the first chamber 105 to pass from the first chamber 105 via the aperture 132 to the second chamber 110, thereby sensing the molecule 170 as it passes through the aperture 132.

In some embodiments, sensing the molecule 170 includes detecting or measuring a change in an electrical parameter associated with generating the electric field 140 as the molecule 170 passes through the aperture 132. In some embodiments, a strength of the electric field 140 at the aperture 132 in combination with a dimension of the aperture 132 causes the molecule 170 to be denatured as it passes through the aperture 132. In some embodiments, sensing the molecule 170 is performed with sufficient sensitivity to discriminate between or among different hairpin compounds passing through the aperture 132. In some embodiments, an organic matter 131 is coupled to the chemical layer 125 at the aperture 132, and wherein sensing the molecule 170 senses the molecule 170 as it passes from the first chamber 105 to the second chamber 110 through a channel 133 defined by the organic matter.

In an example embodiment, a set of hairpins is used with designed sequences that through an efficient restriction enzyme step, DNA hairpins can be cleaved and released from magnetic microbeads. In an example embodiment, long DNA hairpins with restriction sites are located at different distances from the loop, and conjugated to magnetic microbeads through streptavidin-biotin binding. Upon cleavage with a restriction enzyme, DNA hairpins of different length are released into the buffer and detected by a nanopore without any further sample preparation and purification. In an example embodiment, a novel chip-based lipid bilayer support platform with improved lifetimes and higher voltage stability than traditional PTFE apertures, allowing efficient sensing of released hairpins down to nanomolar (nM) concentrations allows for improved detection sensitivity and ensures hairpin unzipping. In an example embodiment, grayscale photolithography (GPL) is used to fabricate ~100 μm wide apertures in SU-8 films that have different 3D profiles. These apertures allow the convenient formation of large-area lipid bilayer membranes for single-channel measurements that are stable for up to 8 hours and routinely sustain applied voltages of 350 mV.

Stable Lipid Bilayer on SU-8 Apertures. A major drawback of biological nanopores is the fragility of the lipid bilayer membranes that support them. Traditionally, a 10-50 μm thick PTFE sheet with a 100-200 μm diameter hole drilled by laser, electrical spark ablation, or mechanical punching is used as an aperture support for lipid bilayer membranes. Generally, the geometries and edge shapes of gaps fabricated using these relatively coarse drilling processes are not accurate and reproducible, often leading to film fragility, inhomogeneous lipid coating, low lipid membrane formation success rate, and short membrane lifetimes. There are a few major avenues for improving the stability of the freestanding membranes: (i) reinforcement of the membrane by replacing biological lipids with synthetic polymers, or by strengthening the lipid bilayer through, for example, chemical conjugation of actin filaments to the bilayer, (ii) support or encapsulation of the lipid bilayer by porous hydrogels, and (iii) improved geometry and surface properties of the aperture. Unlike the first two approaches, which may hinder protein insertion and biomolecule capture, modifying the aperture does not interfere with protein-membrane interactions and does not compromise analyte capture, since the native environment of the protein channel is preserved. Further, decreasing the aperture diameter can further improve the membrane stability, although this compromises the protein channel insertion probability, especially for protein channels that are delivered by proteoliposomes. Another strategy previously reported to improve the stability of lipid membranes is to use thinner apertures or alternatively creating an gap with sharper edges which allows the two lipid leaflets across the gap to meet each other over a smoother curve, thereby forming a bilayer with minimum perturbations caused by solvent annulus fluctuations.

In some embodiments, a method for manufacturing an apparatus, as depicted in FIG. 1A, for sensing a molecule comprises forming a component, also referred to herein as a divider element, for an apparatus for sensing a molecule, forming structural elements, and producing a film of chemical layer. The component 115 decreases in thickness between a first surface 116a of the component 115 and a second surface 116b of the component 115 from a distal location to a proximal location relative to a gap 130 defined through the component 115. The gap 130 extends between the first surface 116a and the second surface 116b. Producing the film of chemical layer 125 includes adhering the chemical layer 125 to the first surface 116a of the component 115 and to the second surface 116b of the component 115 at least proximal to the gap 130.

Figure 2A:
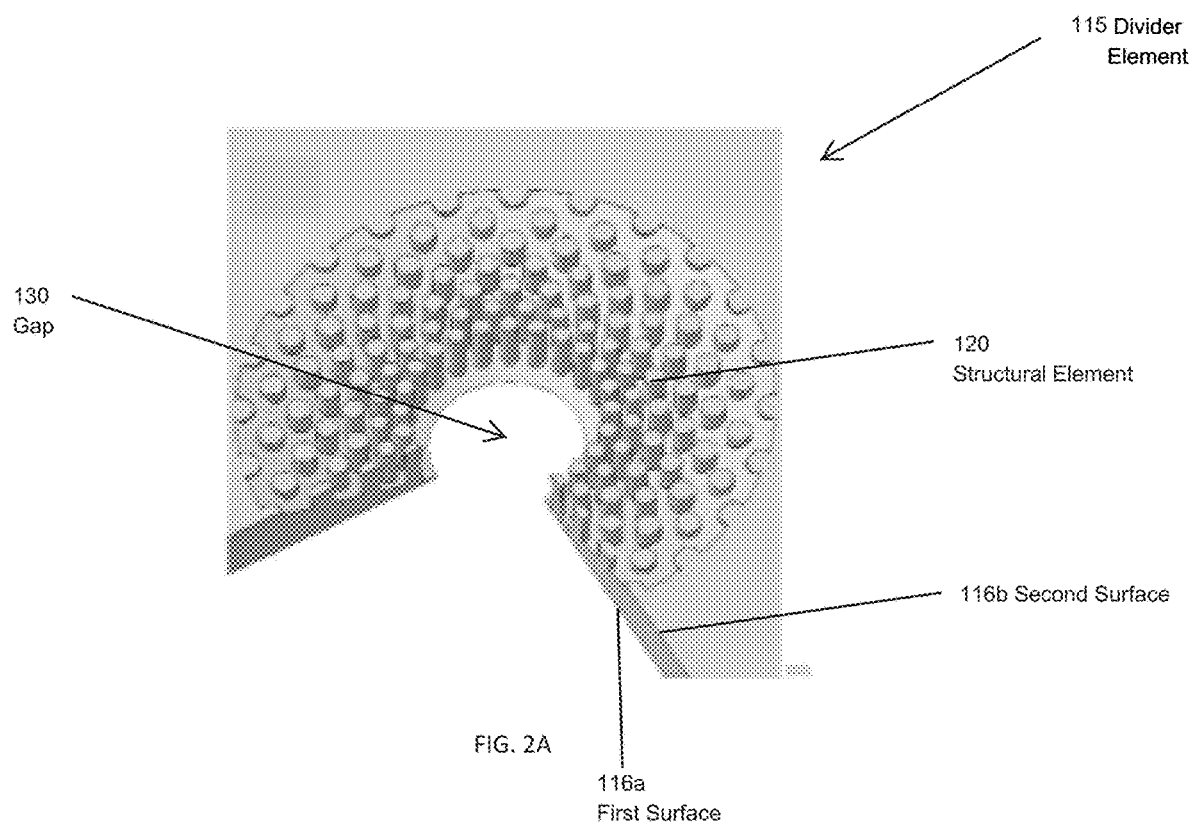
FIG. 2A is a diagram of a component, in accordance with an embodiment of the invention.
Figure 2B:
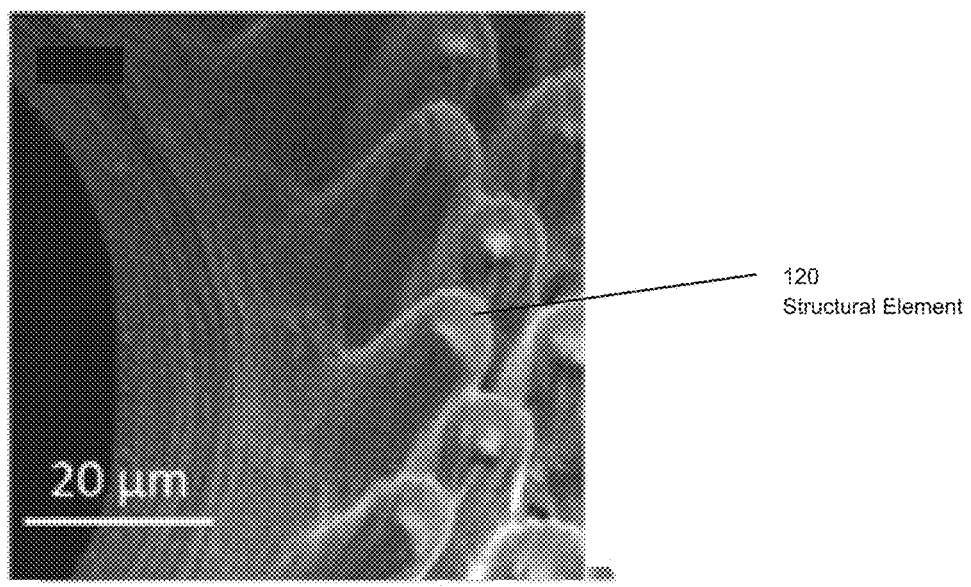
FIG. 2B is a plan view of structural elements on a divider element, in accordance with an embodiment of the invention.
Figure 2C:
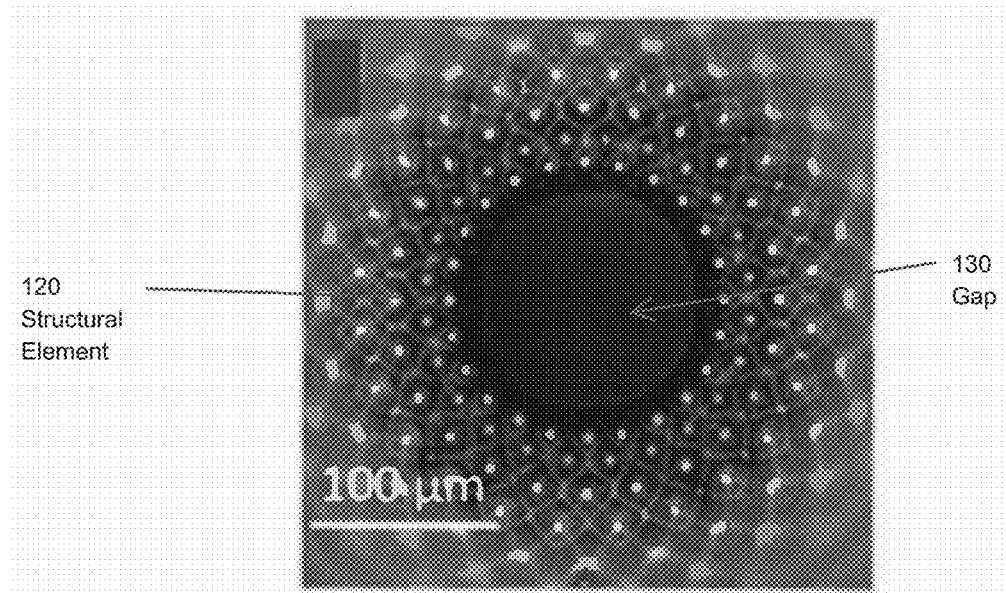
FIG. 2C is a bottom view of structural elements on a component, in accordance with an embodiment of the invention.
Figure 10A:
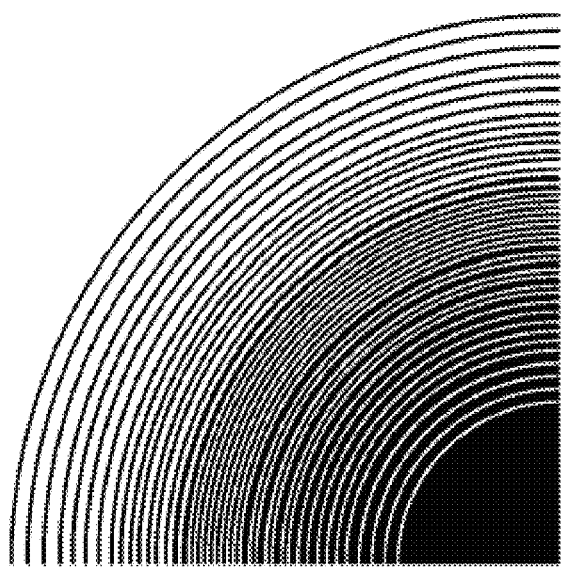
FIG. 10A depicts a wedge shape on a photomask, in accordance with an embodiment of the invention.
Figure 10B:
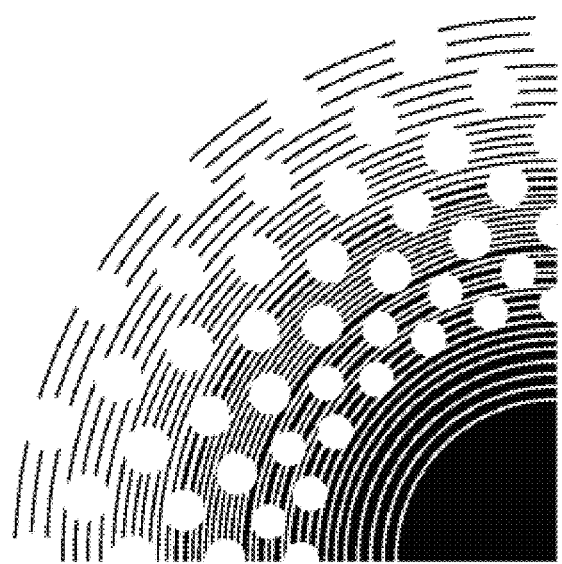
FIG. 10B depicts a pillars-on-wedge pattern on a photomask, in accordance with an embodiment of the invention.
Figure 10C:
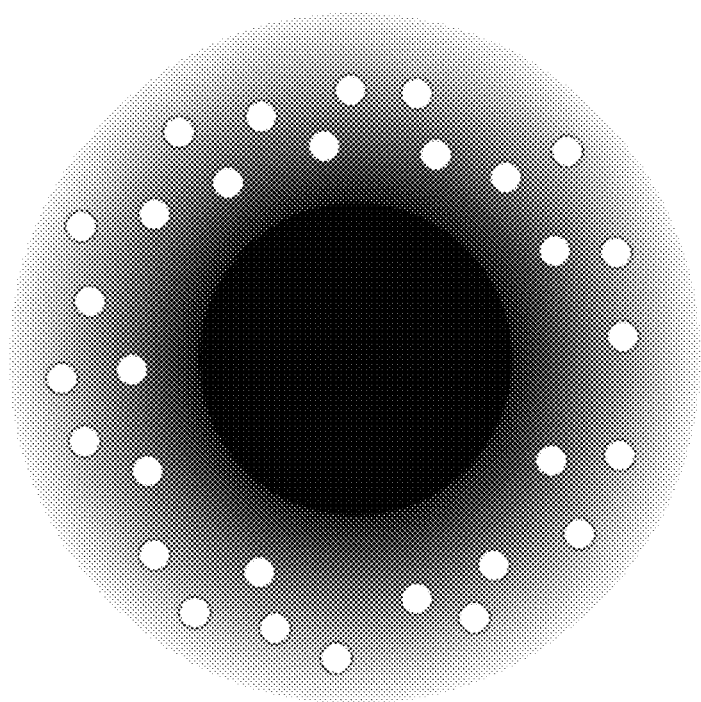
FIG. 10C depicts a pillars-on-wedge pattern on a true gradient mask, in accordance with an embodiment of the invention.

An example embodiment includes a method for scaled-up fabrication of such apertures with sharp edges using GPL. SU-8 is a hydrophobic polymer with low dielectric constant, which makes it a suitable material for lipid bilayer membrane apertures. Furthermore, its compatibility with standard photolithography and its availability in thin layer format (2-200 μm) enables a range of structures to be fabricated. The main advantage of an SU-8 component over commonly-used PTFE components is its smoother edges, as well as the excellent control over the diameter and thickness of the component afforded by the GPL process. There are two important aspects of forming a stable lipid bilayer support: 1) it benefits from a small merging angle (θ) of the two leaflet layers, and 2) solvent drainage during the experiments destabilizes the membrane. Due to geometrical constraints, the commonly used cylindrical apertures suffer from a relatively large merging angle, as seen in FIGS. 9A-D. An example embodiment addresses this problem by taking advantage of GPL to effectively produce a UV exposure dose gradient at the gap, thereby controlling its edge thickness and slope. The resulting gap with a wedge-shaped cross section, as depicted in FIGS. 9E-H, is expected to outperform cylindrical gap, since the two lipid leaflets from the top and bottom of the solvent annulus merge smoothly, with a smaller angle and a minimum perturbation. Moreover, membrane stability could be further improved by creating structures around the wedge-shaped component that provide a solvent reservoir to compensate for its drainage during prolonged experiments. In some embodiments, GPL is used to fabricate a wedge-shaped component surrounded by solvent-pinning pillars. In some embodiments of the method for manufacturing a component, the component is exposed to a light, the light having an intensity configured to increase from a central location of an aperture to an edge location of the aperture. An example of the resulting divider structure is illustrated in the dividers of FIGS. 2A-C, which, as described above, depict a schematic drawing, optical microscope image, and scanning electron microscope image of the divider structure surrounding this gap, respectively. The pillars diameters and spacing are designed to provide an inward capillary force toward the gap's edge. The photomask patterns used for fabricating the wedge-shaped and pillars-on-wedge aperture are depicted in FIGS. 10A-C. All three gaps have been fabricated on a 20 µm thick SU-8 layer, with a target gap diameter of 100 µm, although sometimes there were slightly larger (<10%) final diameters due to underexposure of the patterns.

Figure 2D:
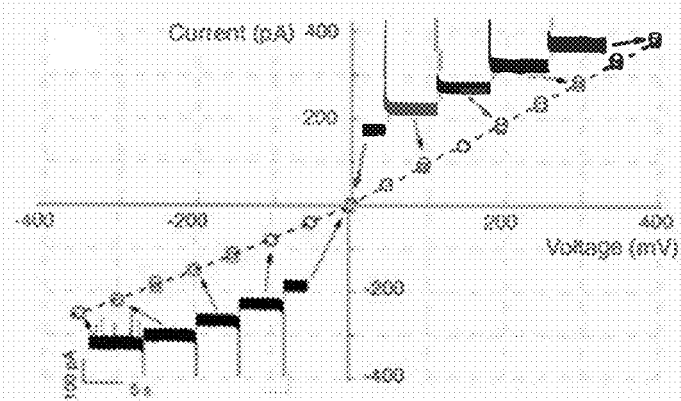
FIG. 2D depicts a current-voltage curve, in accordance with an embodiment of the invention.

Previous studies indicate that α-hemolysin nanopores do not gate at applied voltages below 340 mV, and therefore these channels are prime candidates for high-voltage sensing applications. In an example embodiment, the stability of the membranes formed on SU-8 supports is tested by inserting a single α-hemolysin channel into diphytanoyl phosphatidylcholine (DPhPC) lipid bilayers. Table S1 summarizes the performance of the lipid bilayers suspended on the three gap types under high applied bias. The overall performance of the pillars-on-wedge was observed to be superior to the other apertures, and the bilayers formed in such apertures were able to withstand 350 mV applied bias. Further, this platform shows that α-hemolysin does not gate at voltages as high as 400 mV, as indicated by the current-voltage curve shown for two different channels in FIG. 2D, while for negative bias gating occurs at values of −350 mV, as evidenced by the spikes in the current trace.

Figure 11:
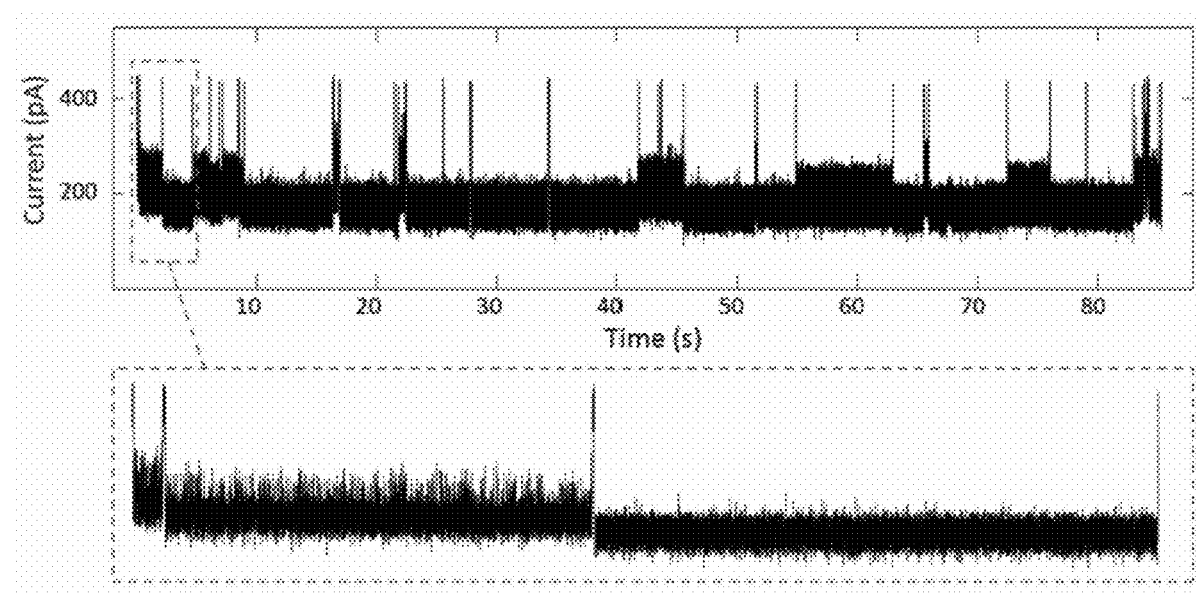
FIG. 11 depicts a current trace of a mixture of 4 bp, 5 bp, and 6 pb DNA hairpins translocating through an α-hemolysin nanopore under 400 mV, in accordance with an embodiment of the invention.

FIG. 11 shows current trace of a mixture of 4 bp, 5 bp, and 6 bp DNA hairpin molecules translocating through an α-hemolysin nanopore being exposed to 400 mV. The experiment depicted by FIG. 11 was performed in 1M KCl, 20 mM Tris, pH 7.6 with a 1 µM total DNA concentration. Data reflected in FIG. 11 was lowpass filtered at 10 kHz. While some example embodiments reflect the ability to record at 400 mV, one may observe leakage current in some devices, as evidenced by increased current baselines and current fluctuations. Nevertheless, the pillars-on-wedge apertures are more stable than the wedge and cylindrical apertures, which withstood lower voltages of 300 mV and 250 mV, respectively, before exhibiting leakage currents and membrane instability. The voltage stability of the cylindrical structure is comparable to the best reported PTFE apertures with the same diameter, while the edge and pillars-on-wedge apertures are superior. Further, a DPhPC lipid bilayer, also referred to herein as a chemical layer, formed on these apertures can last for up to eight hours under <150 mV applied bias after single-channel α-hemolysin insertion. Continuous application of 300 mV applied bias breaks the DPhPC bilayer after 30 minutes. However, intermissions at lower voltage values resolve this problem and significantly increase the membrane's lifetime.

Nanopore Sensing of DNA Hairpins. DNA hairpins are viable reporter molecules for multiplexed nanopore-based sensing. Unzipping dynamics of blunt end, fishhook (one-tail) and internal (two-tail) DNA hairpins in α-hemolysin pores have been extensively explored at low applied voltages (<120 mV). Furthermore, hairpin structures with subtle structural differences, as well as blunt hairpins with even a single nucleotide difference in the stem lengths, produce differentiable current blockades. Other attractive features of DNA hairpins as reporters include their low cost, biocompatibility, thermal stability, high charge density for facilitating capture into nanopores, and finally, their facile and efficient release into solution by cleavage using restriction enzymes. In an example embodiment, the developed lipid bilayer support platform can be used to investigate detection of these molecules at high applied bias, aiming to achieve a higher level of multiplexing, lower LOD values, and improved identification accuracies by enhanced signal-to-noise ratios. Other example embodiments demonstrate a one-pot method for restriction enzyme mediated release of DNA hairpins from a bead and their direct identification without further purification steps.

Figure 4A:
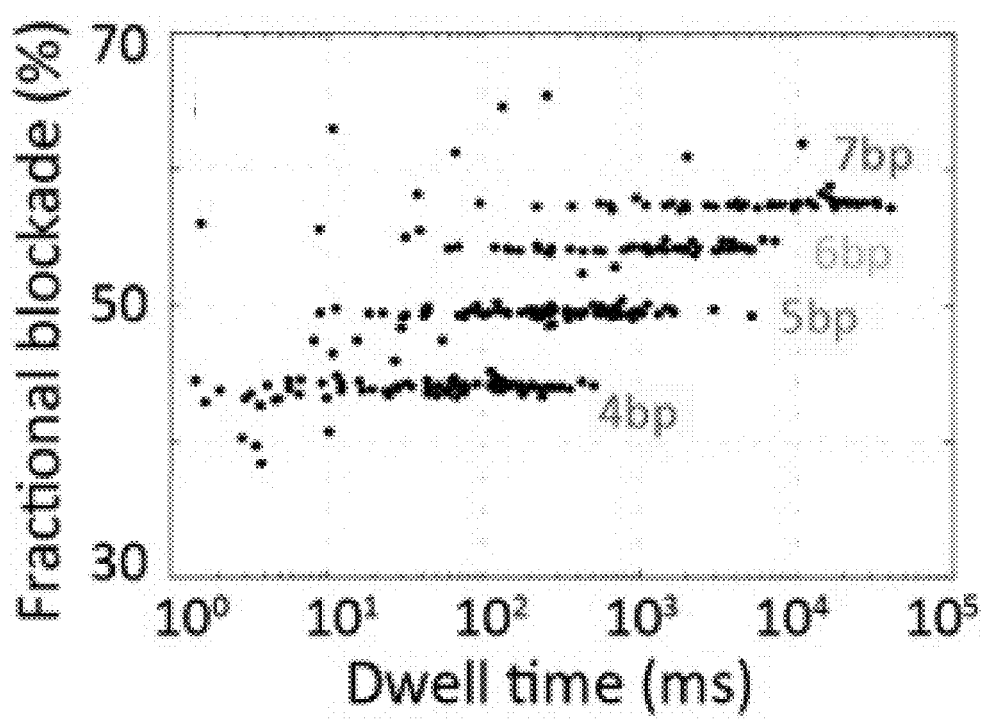
FIG. 4A is a scatter plot of fractional blockade versus dwell time for the four-hairpin mixture, in accordance with an embodiment of the invention.
Figure 4B:
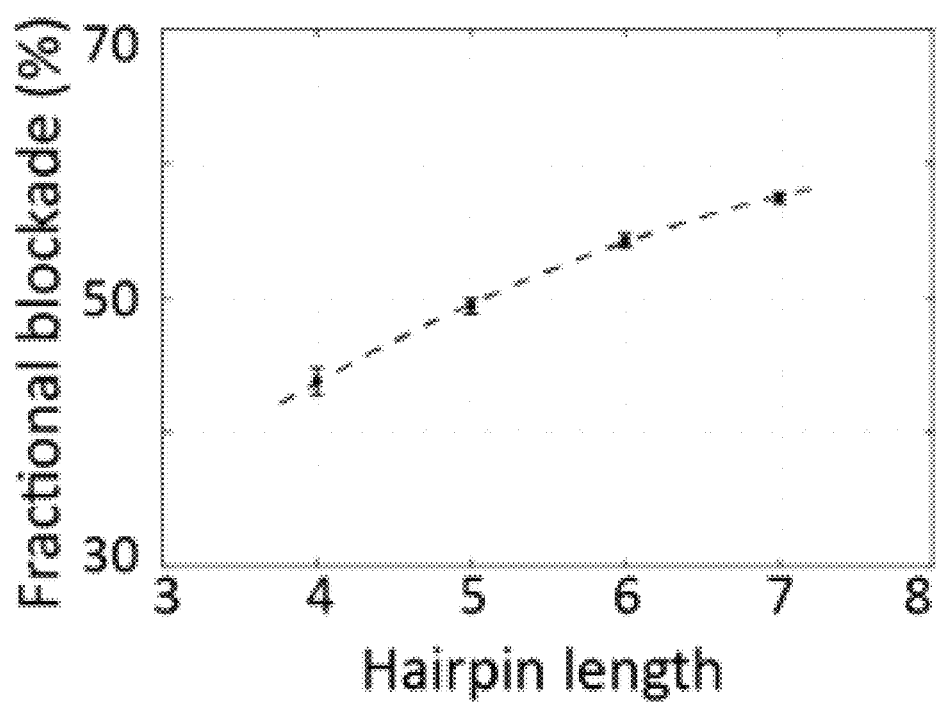
FIG. 4B is a mean fractional current blockade versus hairpin length for the data in FIG. 4A, in accordance with an embodiment of the invention.
Figure 7A:
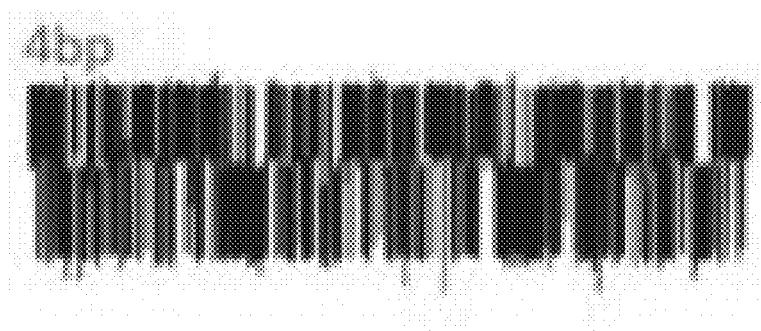
FIGS. 7A-D depict a differentiation of DNA hairpins with different lengths using α-hemolysin nanopores, in accordance with an embodiment of the invention.
Figure 7B:
Figure 7C:
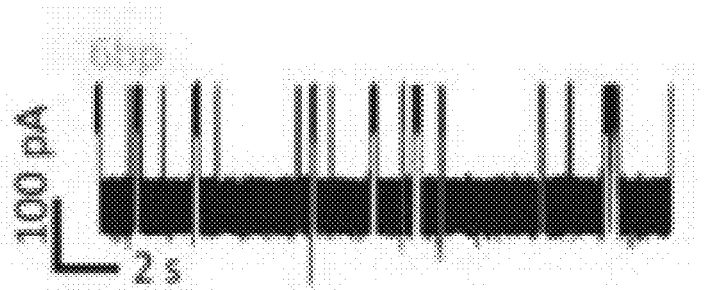
Figure 7D:
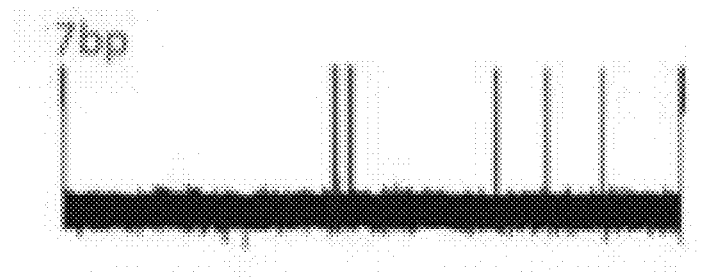
Figure 7E:
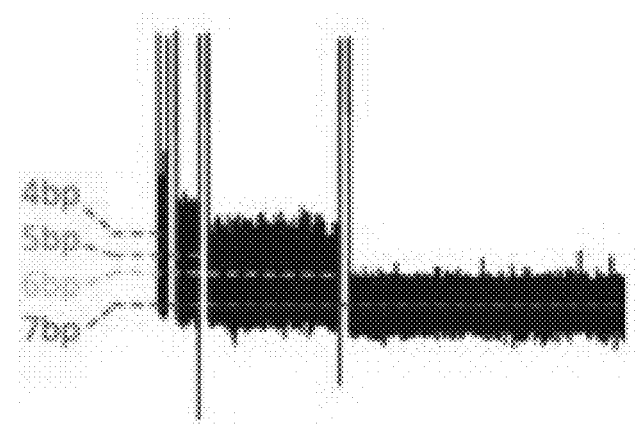
FIGS. 7E-F depicts a continuous current vs. time trace (350 s) showing capture and translocation of a mixture of 4-7 bp hairpins, in accordance with an embodiment of the invention.
Figure 7F:
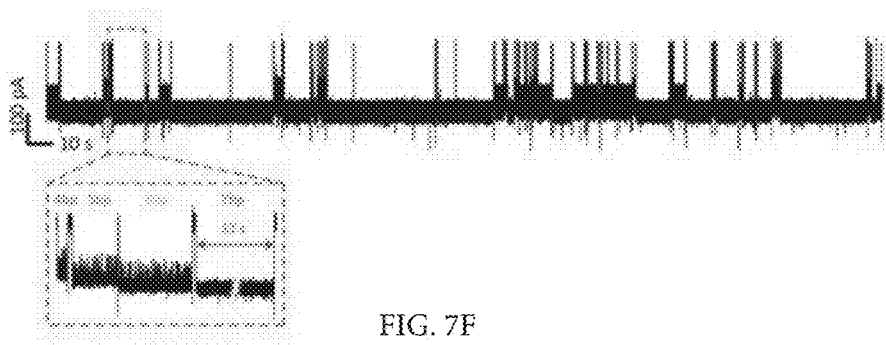
Figure 12:
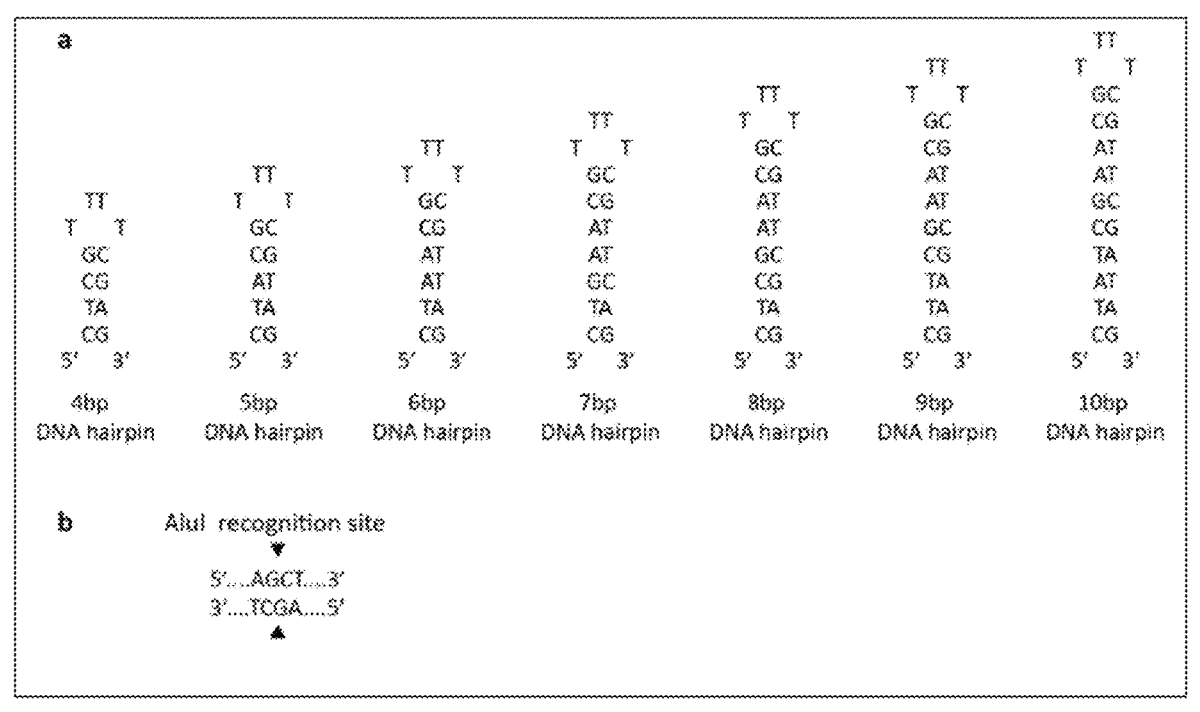
Figure 13:
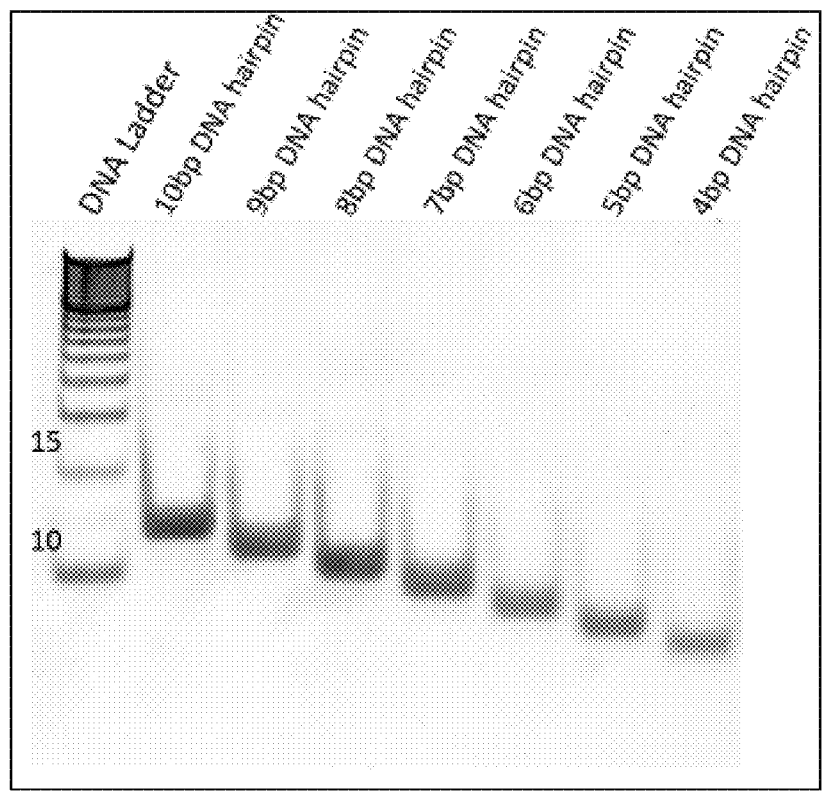
FIG. 13 depicts a native PAGE characterization of DNA hairpin molecules, in accordance with an embodiment of the invention.

The sequences of DNA hairpins used in accordance some embodiments are shown in FIG. 12. DNA hairpin purity was first assessed using 20% native PAGE electrophoresis, as depicted in FIG. 13, which shows that DNA strands have folded into uniform hairpin structures. Example embodiments use the pillars-on-wedge SU-8 component to suspend DPhPC lipid bilayer and insert a single α-hemolysin pore. FIGS. 7A-D show representative current traces of 4 bp, 5 bp, 6 bp, and 7 bp DNA hairpins translocating through an α-hemolysin pore at 300 mV. Comparison of single events from each hairpin length, shown in FIG. 7E, shows distinct current levels and dwell times. Additionally, as previously reported, each event has a characteristic dwell time corresponding to the hairpin being trapped inside the pore vestibule, followed by a sharp deep blockade which indicates hairpin has unzipped and translocated through the pore. This second level for some of the events has not been captured owing to the unzipping timescales being faster than the measurement bandwidth. In some example embodiments, as the stem length increases, the current blockade increases since a larger volume inside the α-hemolysin vestibule is occupied by the hairpin stem. This was further demonstrated by examining simultaneous detection of a mixture of 4 different hairpin lengths. FIG. 7F shows a 350s current trace of a mixture of 4-7 bp DNA hairpins translocation through α-hemolysin recorded at 300 mV. The zoomed-in trace clearly shows four distinct current blockade levels, each associated with a different hairpin. Scatter plot of the current blockade-dwell time clearly demonstrates four distinguishable populations, shown in FIG. 4A and confirms that multiplexed sensing with a mixture of hairpins can be done with high fidelity. Moreover, this plot indicates longer hairpins dwell inside the vestibule for longer times, which points to a higher energy required for unzipping. The large standard deviation of the dwell time distribution evident from the scatter plot is a characteristic of the hairpin unzipping dynamics. Mean fractional current blockades for different DNA hairpin stem lengths, obtained from Gaussian fits, indicates a relationship between fractional blockade and the hairpin length that is best described by a second-order polynomial, as seen in FIG. 4B (dashed line).

Figure 14:
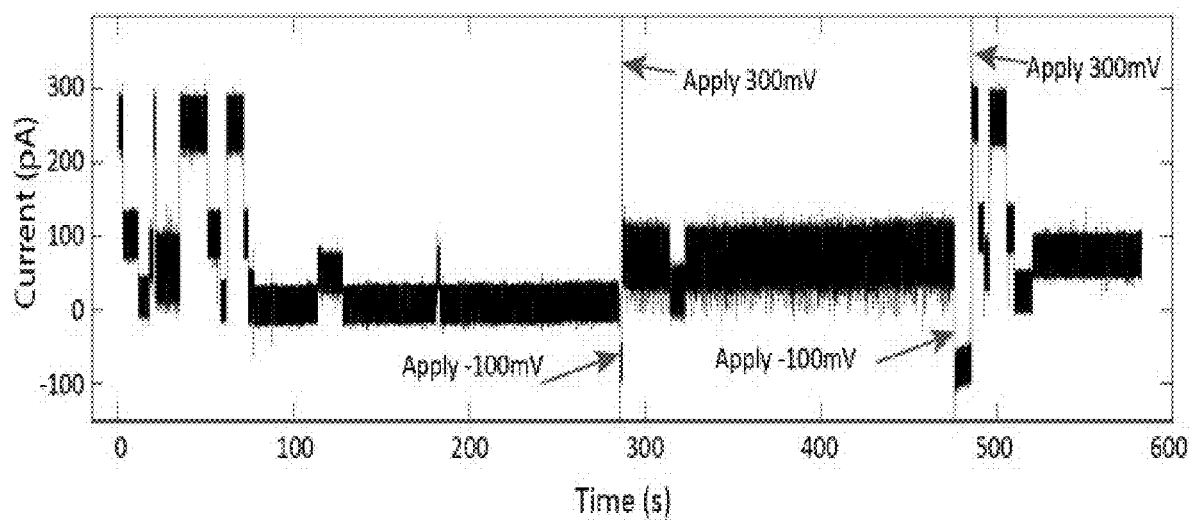
FIG. 14 depicts a current trace of 8 bp of DNA hairpins translocation through an α-hemolysin nanopore under 300 mV applied bias, in accordance with an embodiment of the invention.

Some example embodiments include the possibility of unzipping longer hairpins in α-hemolysin nanopores, as it was previously shown that hairpins longer than 6 bp cannot translocate at 120 mV. Interestingly, in spite of the large applied voltage, DNA hairpins longer than 6 bp still do not smoothly translocate through the pore. In case of the 7 bp hairpins, although they can traverse the pore at 300 mV, their dwell times are very long and can be up to 40 seconds, as seen in FIG. 4A. As for the 8 bp hairpins, the stem length is close to the length of the vestibule and therefore a smaller electromotive force is applied to the loop, while the blunt end of the hairpins is pressed against the pore constriction. 8 bp hairpins may translocate through the pore and sometimes attempt to enter the constriction but cannot translocate, giving rise to multiple current levels, very high blockades (~96%), and long dwell times (>100 s) until they are removed from the vestibule by reversing the voltage polarity, which is depicted in FIG. 14. Some example embodiments restrict multiplexing to three reporter molecules, namely, 4-6 bp hairpins.

Figure 5A:
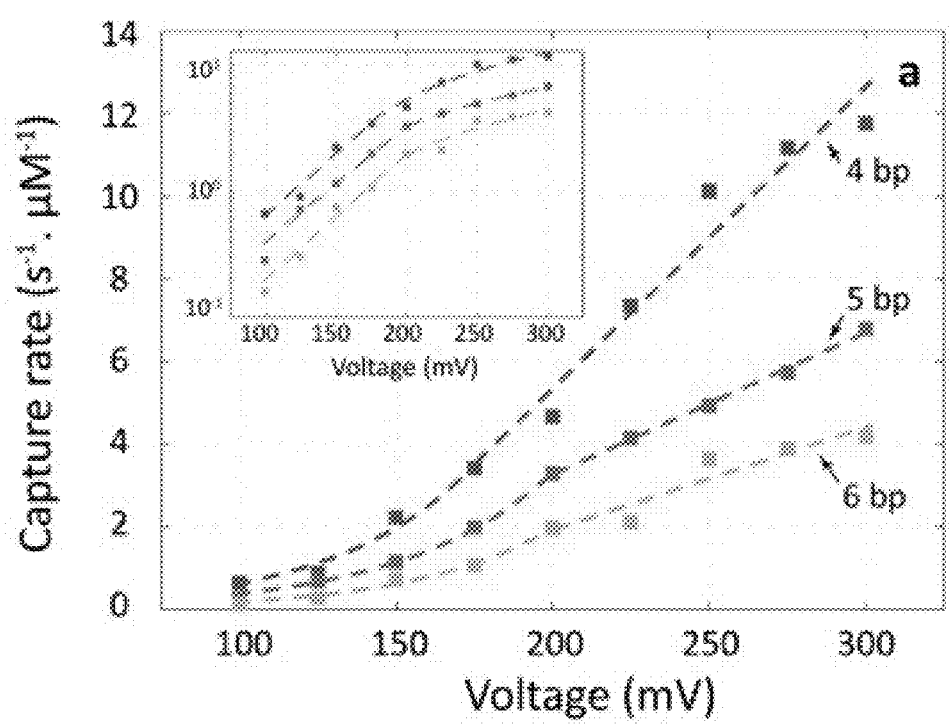
FIG. 5A is a depiction of voltage-dependent concentration-normalized capture rates for 4 bp, 5 bp, 6 bp DNA hairpins, in accordance with an embodiment of the invention.
Figure 5B:
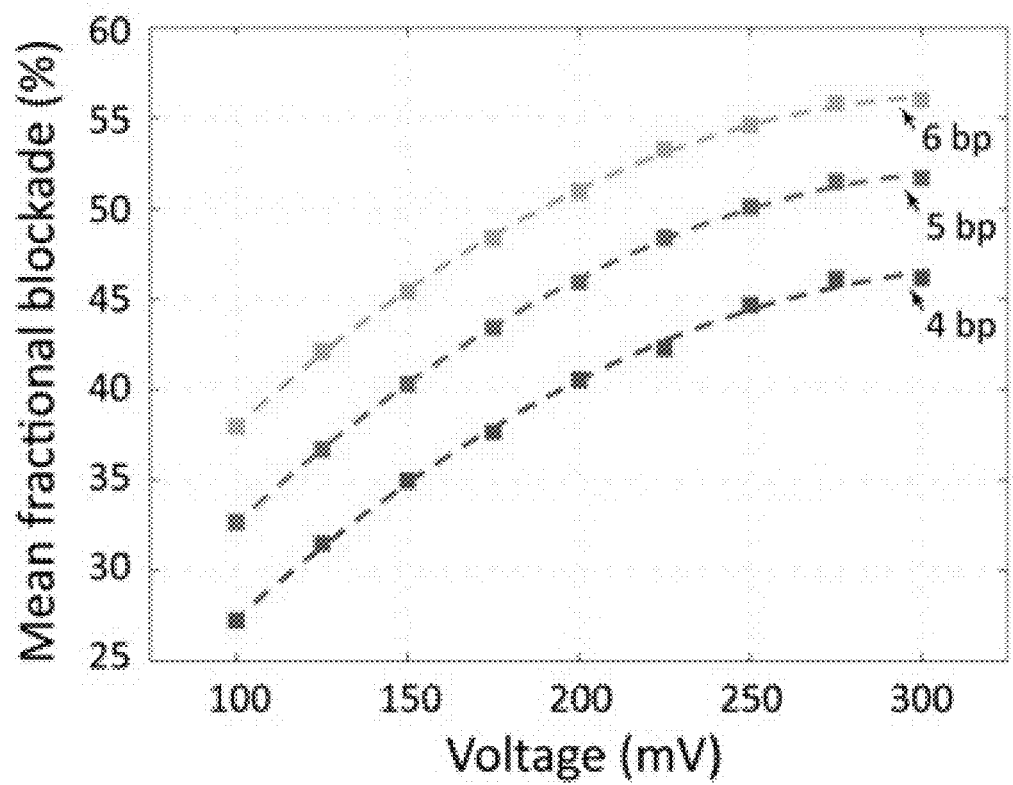
FIG. 5B depicts a mean fractional current blockade for the hairpins depicted in FIG. 5A, in accordance with an embodiment of the invention.

A useful factor in developing a nanopore-based sensitive detection scheme is the capture rate of the species. Studies pertaining translocation of single-stranded DNA through α-hemolysin distinguish two different capture regimes, namely the energy barrier-limited and the diffusion-limited regimes. At small applied bias values, an energy barrier associated with entropic and steric effects limits the entry rate of molecules into the pore. In this voltage regime, the capture rate increases exponentially with applied voltage, suggesting that capture is best described by an Arrhenius equation. In addition, in this regime capture attempt rates, indicated by the offset of the semi-log curves in FIG. 5A, decrease with hairpin lengths. This can be attributed to the smaller diffusion coefficients for longer hairpins, which in turn reduces attempt rates. However, beyond some voltage threshold, hairpin diffusion to the pore's capture zone determines the capture rate. In this regime, capture rate is linearly proportional to the voltage, consistent with the expected linear increase in capture radius with increasing bias. Example embodiments demonstrate a cross-over voltage of 175 mV for the 4 bp hairpin, and ~200 mV for longer hairpins. This value is higher than the cross-over voltage of poly(dC)$_{40}$ single-stranded DNA translocation (i.e., 120-140 mV), which informs on the higher energy barrier associated with tight immobilization of the hairpins inside the pore vestibule. Nonetheless, it is clear from FIG. 5A that the ability to increase the applied bias to 300 mV results in an order of magnitude improvement in capture rate for all three hairpins. These results were obtained with a mixture of hairpins in a single pore to eliminate possible pore-to-pore variation and other experimental errors. Increasing the applied bias increases the mean fractional current blockades, as shown in FIG. 5B. This suggests that a higher applied force can partially squeeze the hairpin loops into the vestibule. An important consequence of this is that signal-to-noise values are further enhanced at the higher voltages.

Figure 6:
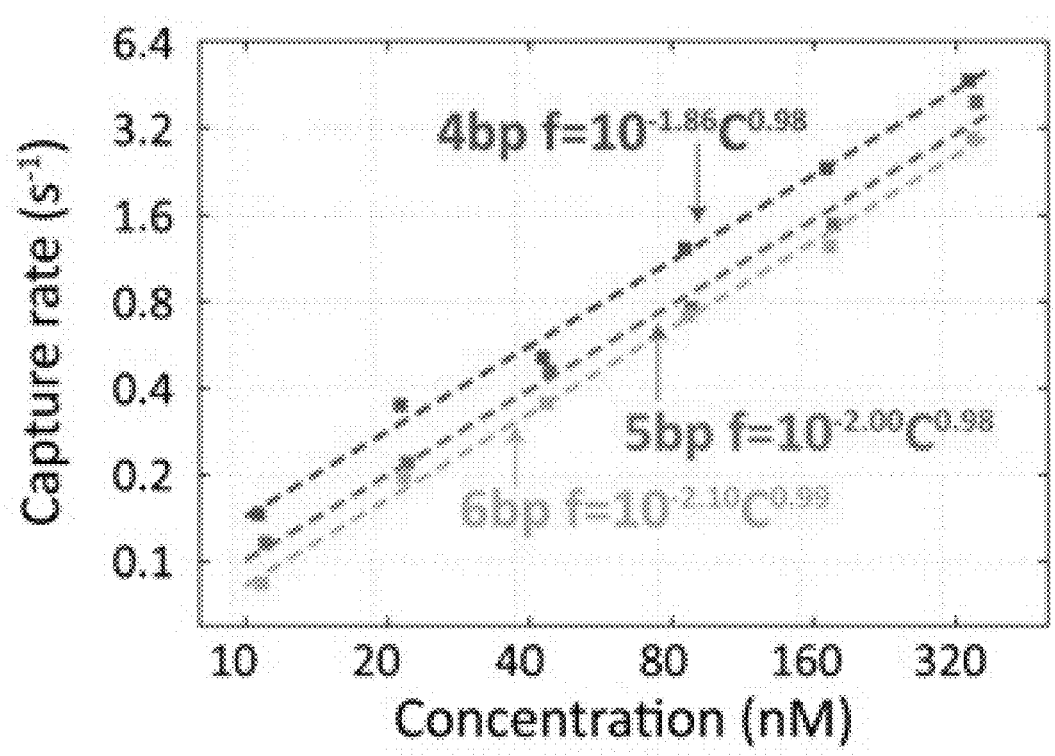
FIG. 6 depicts capture rate as a function of hairpin concentration, in accordance with an embodiment of the invention.

There are practical limits of detection for a mixture of DNA hairpins at different concentrations under high applied bias. Each hairpin had a concentration in the range of 10 to 350 nM. FIGS. 8A-F show the current traces of translocation of hairpin mixtures with different concentrations, at 300 mV. At the lowest concentration, a 10-minute current recording was obtained and a total number of 210 events were detected. Capture rates were extracted by fitting exponential curves to the inter-event time distributions. As the log-log plot in FIG. 6 shows, there is, within error, a good linear dependence between capture rate and concentration for all three hairpins, with exponents of 0.98, 0.98, and 0.99 for the 4 bp, 5 bp, and 6 bp hairpins, respectively. Further, longer hairpins have lower capture rates, as evident in this plot. Importantly, under high applied voltage, detection of these hairpins at few-nM concentrations is practical, with rates in the range of 0.1 s$^{-1}$ for 10 nM hairpin concentrations. Finally, this limit can in principle be pushed further to lower practical LOD values by applying a salt gradient across the pore.

Figure 3:
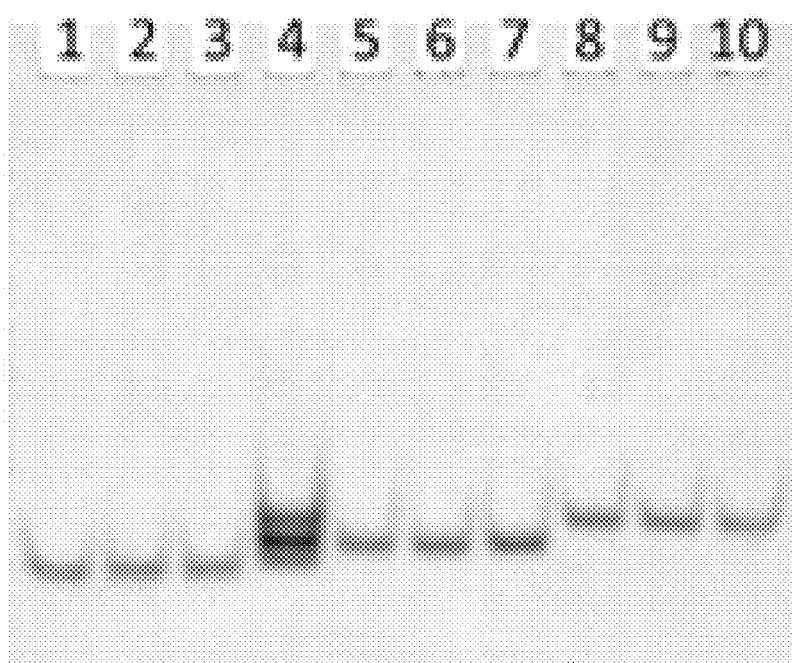
FIG. 3 depicts 20% native polyacrylamide gel electrophoresis (PAGE) gel stained by Gelred®, in accordance with an embodiment of the invention.
Figure 15:
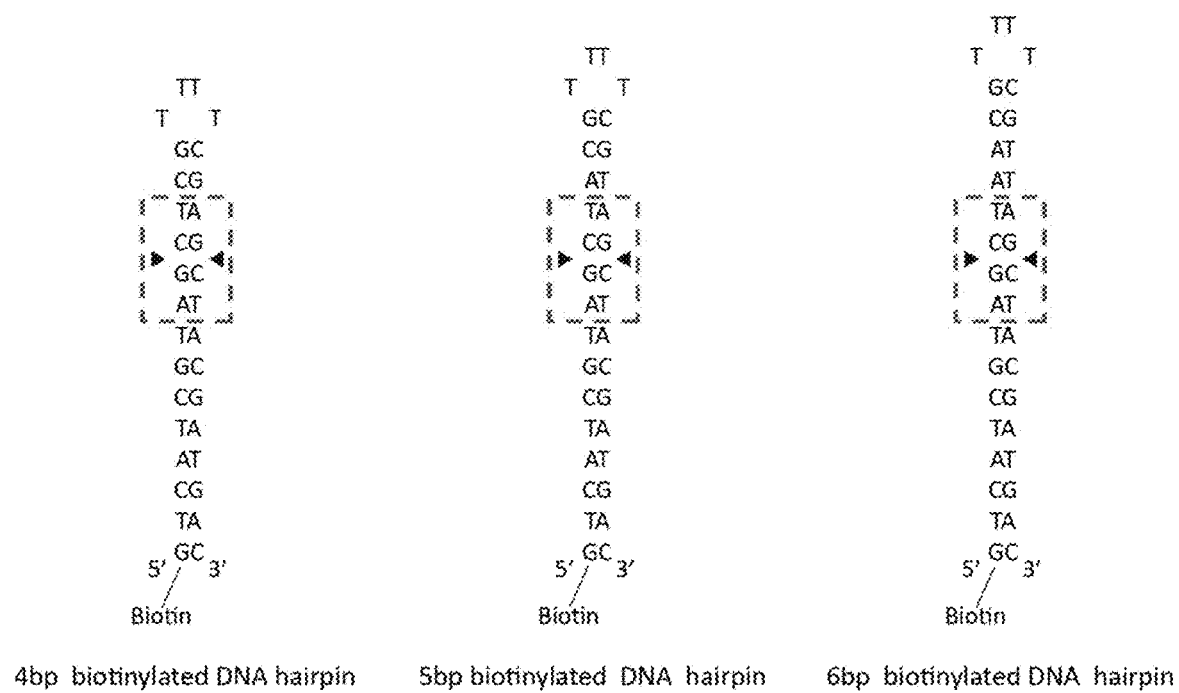
FIG. 15 depicts a sequence of the biotinylated DNA hairpins, in accordance with an embodiment of the invention.
Figure 16:
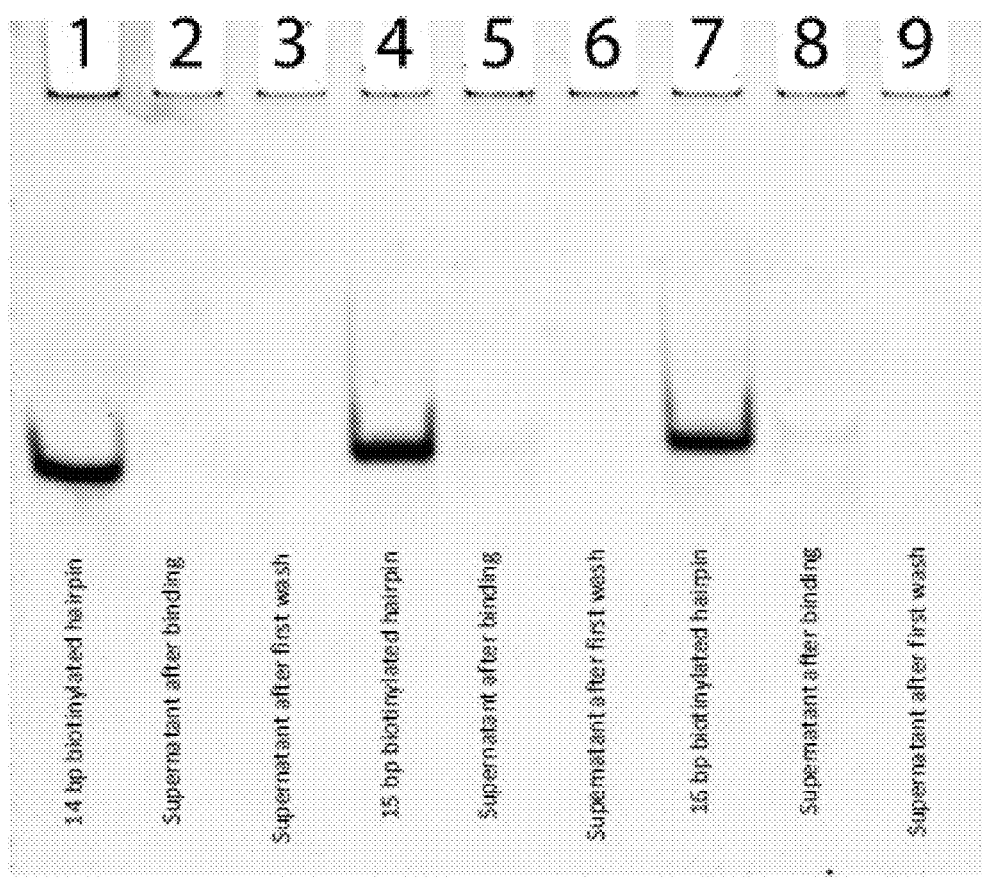
FIG. 16 depicts a native PAGE representation of binding efficiency of biotinylated hairpins to streptavidin-coated magnetic beads, in accordance with an embodiment of the invention.

Enzymatic Release of Reporter Hairpins. In some example embodiment, a system is created whereby hairpins are immobilized on microbeads are released using a simple enzymatic cleavage step, followed by their nanopore-based detection without any purification steps. Longer DNA hairpins can be created by extending 4-6 bp hairpins by 10 bp, such that cutting these extended hairpins using a restriction enzyme releases 4, 5, and 6 bp hairpins with the exact same sequences as used earlier, which is shown in FIG. 15. In fact, the stem end of all DNA hairpins used in the previous section were designed to match the recognition site of the restriction enzyme AluI, an enzyme that can efficiently cut DNA even close to the DNA end, the sequence of which is shown in FIG. 12. FIG. 12 depicts DNA hairpin molecule sequences and the restriction enzyme's recognition site, including possible DNA hairpin molecule sequences and predicted hairpin molecules' secondary structure and an AluI restriction enzyme's recognition site. Further, the 5' ends of the extended hairpins were biotinylated to allow conjugation with streptavidin-coated magnetic beads. The binding efficiency of biotinylated hairpins with the beads was confirmed to be high using native PAGE gel, as depicted in FIG. 16. As shown in FIG. 16, lane 1 is the 14 bp biotinylated DNA hairpin molecules and lanes 2 and 3 are the supernatant after binding and after a first wash. Lane 4 is the 15 bp biotinylated DNA hairpin molecules and lanes 5 and 6 are the supernatant after binding and after a first wash. Lane 7 is a 16 bp biotinylated DNA hairpin molecules and lanes 8 and 9 are the supernatant after binding and after a first wash. By introducing the enzymes, extended hairpins were cut and the reporter molecules were released from the beads, as illustrated in FIG. 1C. Successful cutting of the hairpins, also referred to herein as hairpin molecules, was further verified using native PAGE, as shown in FIG. 3. Cutting immobilized hairpins produced bands corresponding to the 4-6 bp hairpins. Here, when the restriction site is close to the bead surface, the reaction rate is reduced as compared to the free-solution rate for the same molecules, as shown in FIG. 17C. For example, a free-solution reaction time of 3 hours resulted in quantitative short hairpin formation using 10 U enzyme, as shown in FIG. 17B, while in contrast, 60 U enzyme were needed to maximize the cutting yield of hairpins from beads.

Figure 17A:
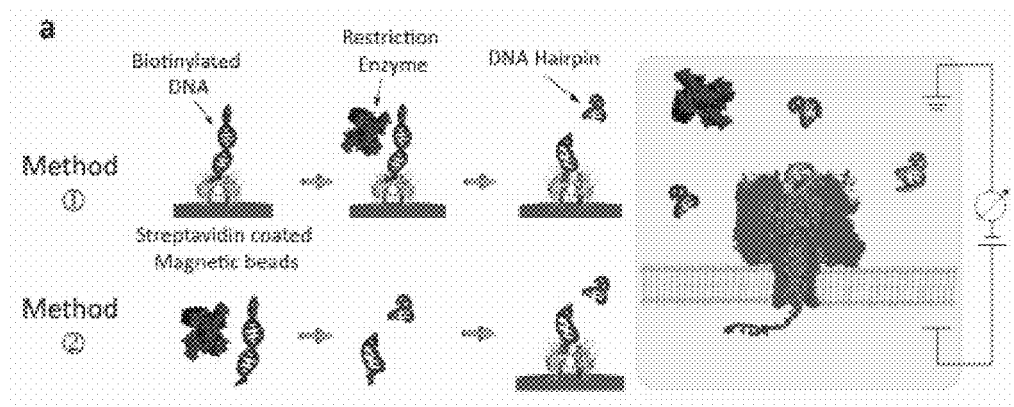
FIG. 17A depicts a schematic of releasing and collecting DNA hairpin molecules using a restriction enzyme and magnetic beads, in accordance with an embodiment of the invention.
Figure 17B:
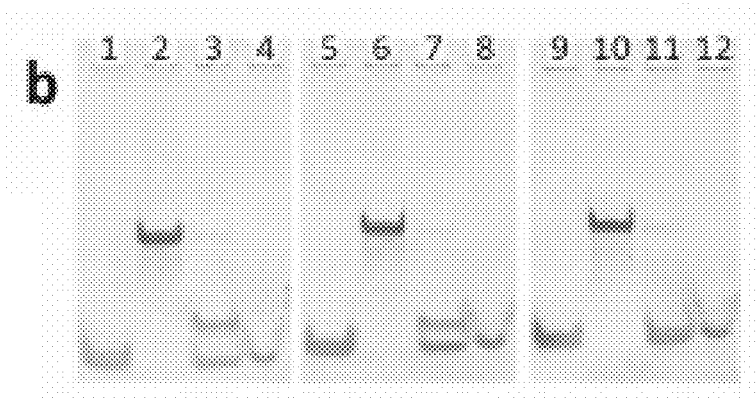
FIGS. 17B-C depict a comparison of 10-unit enzyme digestions of the DNA substrates using the methods depicted in FIG. 17A, in accordance with an embodiment of the invention.
Figure 17C:
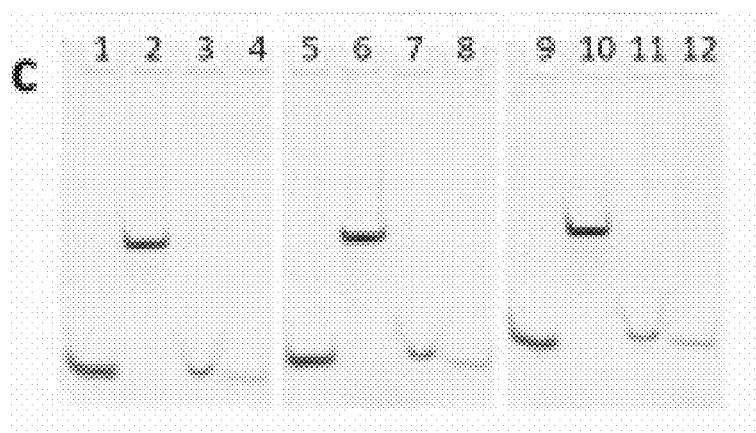

FIGS. 17A-K depict the enzymatic release and direct sensing of the reporter hairpins. FIG. 17A depicts schematics of releasing and collecting DNA hairpin molecules using a restriction enzyme and magnetic beads using two different methods. FIG. 17B depicts a 10-unit enzyme digestion of DNA substrates after 3 hours using Method 2 of FIG. 17A. Lanes 1-4 show: 4 bp DNA hairpins, 14 bp biotinylated DNA hairpins, 14 bp biotinylated DNA hairpins after enzyme digestion, and magnetic bead clean-up of the digested 14 bp hairpins. Lanes 5-8 show: 5 bp DNA hairpins, 15 bp biotinylated DNA, 15 bp biotinylated DNA after enzyme digestion, and magnetic bead clean-up of the digested 15 bp hairpins. Lanes 9-12 show: 6 bp DNA hairpins, 16 bp biotinylated DNA hairpins, 16 bp biotinylated DNA hairpins after enzyme digestion, and magnetic bead clean-up of digested 16 bp biotinylated DNA hairpins. The results semi-quantitively show that the substrates are almost completely digested. FIG. 17C shows a comparison of enzyme cutting efficiency between the two methods with 10-unit enzymes. Lanes 1-4 show: 4 bp DNA hairpins, 14 bp biotinylated DNA hairpins, cutting 14 bp biotinylated DNA hairpins free-in-solution and clean-up using beads, and cutting DNA hairpins immobilized on the beads. Lanes 5-8 show: 5 bp DNA hairpins, 15 bp biotinylated DNA, cutting 15 bp biotinylated DNA hairpins free-in-solution and clean-up using beads, and cutting DNA immobilized on the beads. Lanes 9-12: 6 bp DNA hairpins, 16 bp biotinylated DNA hairpins, cutting 16 bp biotinylated DNA hairpins free-in-solution and clean-up using beads, and cutting DNA immobilized on the beads. FIGS. 17D-K show scatter plots of a fractional current blockade versus dwell time for all eight combinations of the three hairpins in a mixture. The binary code on each plot indicates the presence or absence of the corresponding hairpin in the mixture. Experiments were performed at 300 mV in 0.66 M KCl, 0.33 M NaCl, 20 mM Tris, pH 7.6 buffer. Data was lowpass filtered at 10 kHz.

Since enzyme cutting introduces foreign species to the analyte solution, such as AluI and BSA (bovine serum albumin), one may test for potential interference of these species with the expected hairpin signals. To do this, one may test the reaction solution after enzymatic release from beads without any purification steps FIG. 4C. Importantly, despite the presence of these proteinaceous contaminants, all hairpins in the mixture can one can reliably be sensed and differentiated. Data presented in this FIG. 4C was obtained from a four-minute long recording, with the immobilized hairpin concentrations of $C_{4\ bp}$=90 nM, $C_{5\ bp}$=130 nM, and $C_{6\ bp}$=160 nM on the beads. The measured hairpin concentrations obtained by looking up their capture rates in FIG. 6 and FIGS. 8A-F, are $C_{4\ bp}$=51 nM, $C_{5\ bp}$=83 nM, and $C_{6\ bp}$=95 nM which are 35-40% lower than the expected values. This suggests incomplete release of the hairpins from the beads by restriction enzymes, which requires further quantification and calibrations. However, since the hairpins are first immobilized on beads, their concentrations can be effectively increased by reducing the volume of the release solution, thereby allowing sample pre-concentration for improved LOD values.

An example embodiment explores an alternative, in which the reporter hairpins can be more efficiently detected employs a free-solution cutting of the hairpins, followed by uptake of the biotinylated 10 bp dsDNA stems onto streptavidin-coated magnetic beads. This method shows a high cutting efficiency and requires less enzyme units. An analogous experiment with BglII can serve as a negative control, wherein an enzyme whose restriction site sequence does not match the sequence of hairpins. Nanopore measurements (10 min) shown in FIG. 4C reveal rare sporadic spikes with random current blockade levels and dwell times, unlike the clear populations formed by the released DNA hairpins shown in FIG. 4C. These sporadic events, which result from protein interactions with the pore, are further exemplified by a second negative control experiment where the enzymatic reaction was performed with no DNA substrate immobilized on the beads FIG. 4C. These protein-pore interactions, which only occur at 300 mV bias, are not present at a 200 mV bias.

Demonstrated in an example embodiment herein is a multiplexed biosensing scheme based on enzymatic release of reporter DNA hairpins from microbeads. Stability of the lipid bilayers on the SU-8 apertures was essential in achieving practical detection from nanomolar-level concentrations. The on-chip SU-8 apertures are conveniently and massively produced on a wafer-scale, and the chip form factor is compatible with optical measurements, e.g., for optoelectronic tracking of ion channels, as well as compatible with further elaboration using lithography, e.g., design of on-chip fluidics for low-volume sample analysis. Use of restriction enzymes as a scheme to release reporter molecules is not only compatible with wet-lab molecular biology assays, but also benefits from the sequence specificity and plurality of restriction enzyme choices, which enable further multiplexing. For example, an alternative multiplexing method would be to, instead of sensing different reporter molecules, use the same hairpin lengths with different cutting site sequences and release them using different enzymes. The results obtained inspire a new modality for biochemical data storage using DNA hairpins and reading them using nanopores (Supporting information, section V). In this scheme, each hairpin could be viewed as a bit which can take multiple values based on its concentration. If N is the number of differentiable concentrations by the nanopore and m the number of hairpins that can be differentiated based on their current blockade or dwell times, then a small drop of a hairpin mixture can be defined as a data byte which can assume a value between 0 to ($N^m-1$). Therefore, by creating a nanopore-integrated droplet manipulator, information stored in droplets of hairpin mixtures can be retrieved. Furthermore, data encryption is possible via release of hairpins with a unique restriction enzyme. This proposal can open an avenue for long term data storage and cryptography using DNA and other nanopore-readable biomolecules.

Methods

Fabrication of SU-8 apertures. The SU-8 apertures were fabricated on a 500 μm thick <100> Si wafer that contains a 2 μm thick wet thermal $SiO_2$ layer prior to coating with a 50 nm thick silicon nitride layer. The buried $SiO_2$ layer serves to reduce the capacitance of chips. The wafer, also referred to herein either as a divider element or a component, was patterned to expose an array of 1 mm squares using standard photolithography, followed by $SF_6$ reactive ion etching at 150 W for 2 min to etch the silicon nitride. Next, the silicon dioxide layer was removed using buffered oxide etch (BOE) for 45 min, while the back surface of wafer was protected from the BOE etchant using a single side etcher. A 2010 SU-8 film was spun-coat on the other surface of the wafer at 1000 rpm for 60s, soft baked at 95° C. for 5 min, and exposed with constant power at 275 W for 12s. Grayscale photolithography was used to create wedge-shaped and pillars-on-wedge shaped apertures, as shown in FIGS. 10A-C. After exposure, wafer was post-baked at 95° C. for 5 min and developed for 4 minutes. Next, using single side etcher, the silicon wafer was anisotropically etched using KOH while the wafer back surface was protected, and finally, the $SiO_2$ and the silicon nitride layers were etched with BOE for 45 min and $SF_6$ reactive ion etching at 150 W for 2 min.

Lipid bilayer painting and nanopore measurement. The SU-8 component was first pretreated with 1 μl DPhPC (Avanti Polar Lipids) (5 mg/ml) dissolved in hexane on each side of the membrane. After the hexane evaporated, the chip was mounted on a custom designed flow cell and the cis and trans chambers were filled with 1M KCl, 20 mM Tris, pH 7.6 electrolyte. A pair of Ag/AgCl electrodes were inserted to the chambers and connected to an Axon 200B patch-clamp amplifier to measure the ionic current. Lipid bilayer was painted across the gap using 20 mg/ml DPhPC dissolved in decane. After lipid bilayer formation, 0.5 μl of 5 μl/ml α-hemolysin (Sigma-Aldrich) was added to the cis chamber until a single channel insertion was observed. DNA hairpin samples were added to the cis chamber and mixed gently using a pipette. Current signals were collected at sampling rates of 250 kHz, lowpass filtered to 10 kHz, and analyzed using Python, a software developed for analyzing nanopore signals.

Enzymatic release of hairpins. All oligonucleotides were purchased from Integrated DNA Technologies (IDT) and the restriction enzyme AluI was purchased from New England Biolabs (NEB). A suspension of 25 μl of 10 mg/ml magnetic beads (Dynabeads M-270 Streptavidin, Invitrogen) was transferred to a clean PCR tube and washed with 25 µl 2× Binding&Washing Buffer (2M NaCl, 1 mM EDTA, 10 mM Tris-HCl, pH 7.5) 3 times with gentle pipetting. 50 µl of the 2× Binding&Washing was added to make the bead concentration 5 mg/ml. Next, 50 µl of 20 ng/µl DNA substrate (1 µg DNA) was added to the beads and incubated at room temperature for 30 min while gently shaking the tube using an incubated tube rotator (Roto-Therm™). After DNA conjugation, beads were washed with 1× Binding&Washing Buffer for 2 times and again once with 1× CutSmart Buffer (50 mM potassium acetate, 20 mM Tris-acetate, 10 mM magnesium acetate, 100 µg/ml BSA). The supernatant was removed and saved for a binding efficiency test. The enzyme digestion experiment was performed with 20 U, 40 U, 60 U AluI enzyme in 50 µl final volume of 1× CutSmart Buffer and incubate at 37° C. for 3 hours, while gently shaking. After enzyme digestion, beads were separated using a magnet, and the supernatant was mixed with desired amount of 4 M KCl buffer (20 mM Tris, pH 7.6) so that the final KCl concentration is 1M. DNA hairpins were characterized using 20% native PAGE. All gels were run at 150 V for 1 h, stained with Gelred, and visualized with a Biorad PharosFX imaging system.

Example Embodiment: an example embodiment is a method to produce a graded gap in a polymeric material using grayscale photolithography (GPL). While this process to form angled apertures can be useful for various applications, an embodiment of the invention presents a new application in which pillars-on-wedge apertures are manufactured to support lipid membranes for electrophysiology experiments. Lipid membranes are widely used in the pharmaceutical industry and research arenas, because they allow, for example, to study the impact of various drugs on protein channels, which are often drug targets. In fact, this field is so large for pharma and basic research that companies are starting to produce platforms for automating lipid supports. One distinguishing feature of the lipid support disclosed herein is that the angles and pillared structure affords a higher stability for the lipid membranes than the type of gap that others are producing.

Example Features: The pillared wedged gap is unique in structure.

Example Advantages: Easy formation of highly stable lipid membranes, high voltage stability, longevity of the lipid membranes exceeds state-of-the-art, and scalability of the process to produce the chips.

Example Uses: Improved support gap for electrophysiology experiments, which are used worldwide.

One example potential application of embodiments of this technology is life as a replacement for the current micro electrode cavity array (MECA) chip sold by lonera/Nanion.

Example advantages of embodiments include longer-life measurements and production of more reliable electrophysiology data. The apertures disclosed herein are more stable than others.

Related patents: 1) Systems and methods for biological ion channel interfaces, Kenneth L. ShepardJacob, RosensteinSiddharth, RamakrishnanJared Roseman, US20150090588A1 2) Method for fabricating at least one gap with shaped sidewalls in a layer of a light sensitive photopolymer, Hywel MorganSumit, KalsiMaurits de Planque, Kian Shen Kiang, US20160062239A1 3) Method of fabricating a membrane having a tapered pore, Oliver Harnack, Jurina Wessels, Akio Yasuda, James Clarke, Terry REID, U.S. Pat. No. 8,663,780B2, U.S. Pat. No. 8,137,569B2 4) Planar lipid bilayer array formed by microfluidic technique and method of analysis using planar lipid bilayer, Shoji Takeuchi, Hiroaki Suzuki, Sadao Ota, Wei-Heong Tan, U.S. Pat. No. 8,513,165B2 5) Microfabricated apertures for supporting bilayer lipid membranes, David M. Bloom, Mark C. Peterman, Jonathan M. Ziebarth, U.S. Pat. No. 6,863,833B1.

The SU-8 Apertures and their Performance

TABLE 1

Summary of the performance of lipid bilayers suspended on different apertures under high applied bias. All experiments were conducted with single hemolysin insertion with 1M KCl, 20 mM Tris, pH 7.6. Generally, lipid bilayers do not suddenly rapture under high applied voltage, rather they become leaky, which is characterized by increase in noise and unstable baseline. The results in this table were obtained with at least 6 repeats for each aperture.

| | Cylindrical | Wedge-shaped | Pillars-on-wedge |
|---|---|---|---|
| 250 mV | Good | Good | Good |
| 300 mV | Random current leakage | Good | Good |
| 350 mV | Current leakage | Random current leakage | Good |
| 400 mV | Current leakage/rupture | Current leakage | Random current leakage |

An Alternative Approach to Releasing the Hairpins

Figures 1, 4C:
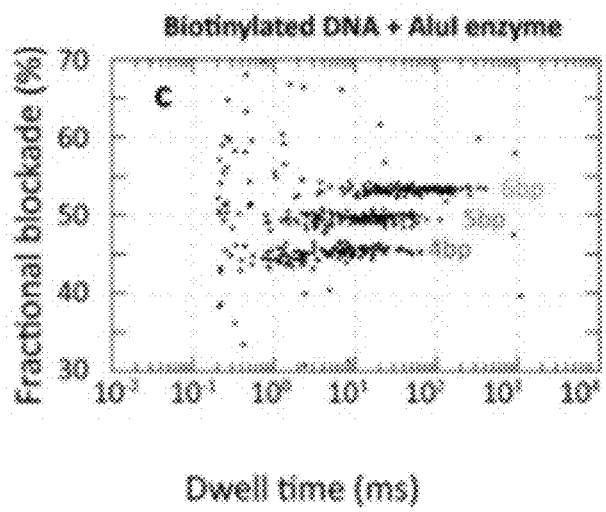
FIG. 4C-1 is a scatter plot of fractional current blockade versus dwell time obtained from analysis of a four-minute recording of a hairpin mixture cut from the beads using the AluI enzyme, in accordance with an embodiment of the invention.
Figures 2, 4C:
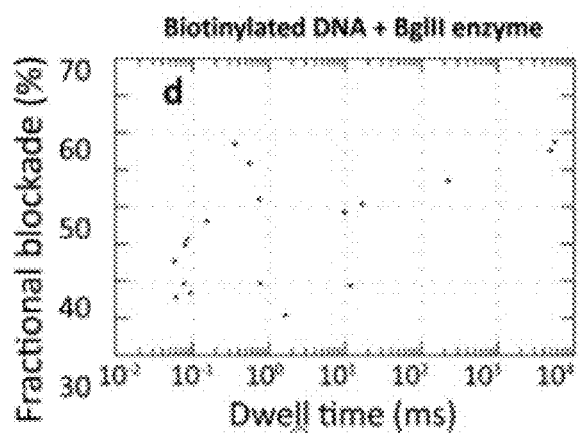
Figures 3, 4C:
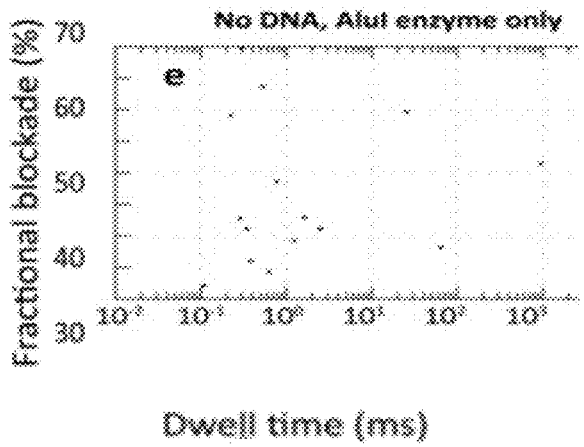

The reduced capture rates obtained in FIG. 4C suggest the proximity of the restriction site to the beads surface hinders enzyme binding or cutting, and therefore enzyme concentration can be increased to expedite release of the reporter hairpins. There is an alternative approach for releasing the hairpins that does not require conjugating DNA hairpins with the beads and therefore is more efficient. In this method, the biotinylated DNA hairpins are first cleaved by the restriction enzymes and then the streptavidin coated magnetic beads are only used to collect the 10 bp dsDNA stems, as shown in FIG. 17A. To do so, 1 µg of the biotinylated DNA hairpins was cut with 10 U AluI in 50 µl 1× CutSmart Buffer (50 mM Potassium Acetate, 20 mM Tris-acetate, 10 mM Magnesium Acetate, 100 µg/ml BSA). After enzyme digestion at 37° C. for 3 hours, 50 µl of the digested hairpins was added to the beads (after 3 time washing) and incubated at room temperature for 30 min with gentle shaking. The digested hairpins before and after clean-up were run through 20% PAGE, as shown in FIG. 17B. Lanes 1 and 2 show 4 bp DNA hairpins and 14 bp biotinylated DNA hairpins. Lane 3 which shows two distinct bands exhibits the 14 bp biotinylated DNA hairpins after enzyme digestion. As it can be seen, the 14 bp band is almost completely cleared which indicates a complete reaction. Finally, in lane 4 the magnetic bead clean-up of the digested 14 bp hairpins is shown. These results verify successful cutting of the DNA hairpins and removal of their 10 bp stems from the sample. Similar results for the 15 bp and 16 bp biotinylated hairpins are presented in lanes 5 thru 8, and 9 thru 12, respectively. The efficiency of this method compared with cutting immobilized hairpins (FIG. 17A) is shown in FIG. 17C. Lanes 1 and 2 show the 4 bp hairpins and the 14 bp biotinylated hairpins. Lane 3 is the 4 bp hairpins obtained following Method 2 (cutting followed by beads clean-up), and finally lane 4 is the 4 bp hairpins obtained using Method 1 (direct cutting from beads). 10 units of enzymes were used for both reactions. The stronger intensity of the third lane indicates higher cutting efficiency of free-in-solution molecules. The distorted band in lane 3 is caused by the 1M NaCl in the magnetic beads binding buffer. Similar results for the 15 bp and 16 bp biotinylated hairpins are presented in lanes 5 thru 8, and 9 thru 12, respectively. 8 different samples are prepared using Method 2, each of which containing a combination of the three reporter molecules immobilized on the beads, and binary coded them with 3 bits. For example, 101 means the sample containing only 4 bp and 6 bp hairpins. These samples were run through α-hemolysin nanopores with no purification step. The scatter plots of the fractional current blockade versus dwell time verifies applicability of this method for release and detection of the reporter hairpins.

Implications for Chemical Data Storage

Figure 8A:
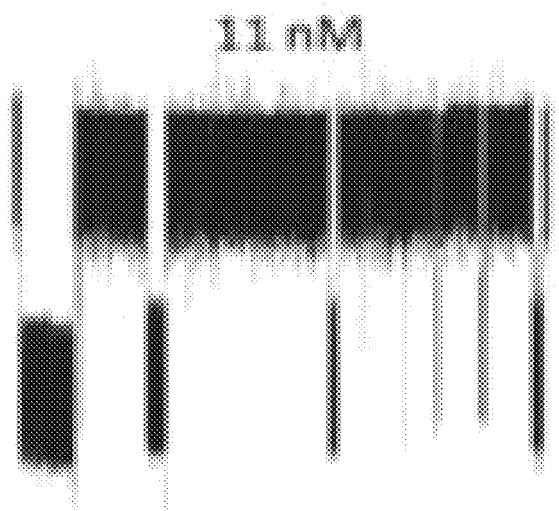
FIGS. 8A-F depict current traces recorded with a mixture of 4 bp, 5 bp, and 6 bp DNA hairpins at different concentration (indicated values are for each hairpin in the mixture), in accordance with an embodiment of the invention.
Figure 8B:
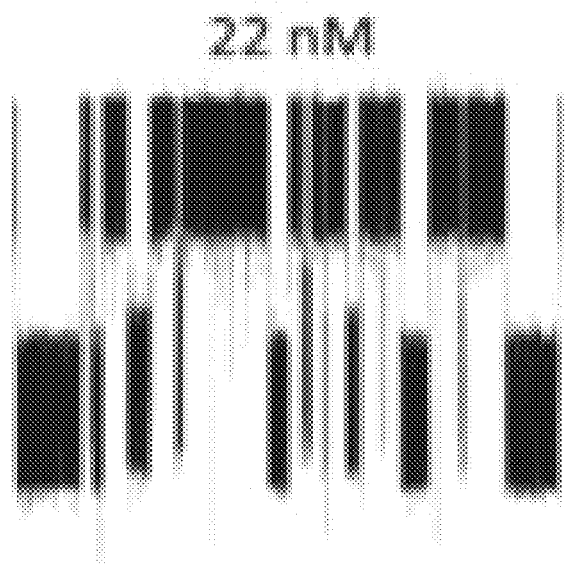
Figure 8C:
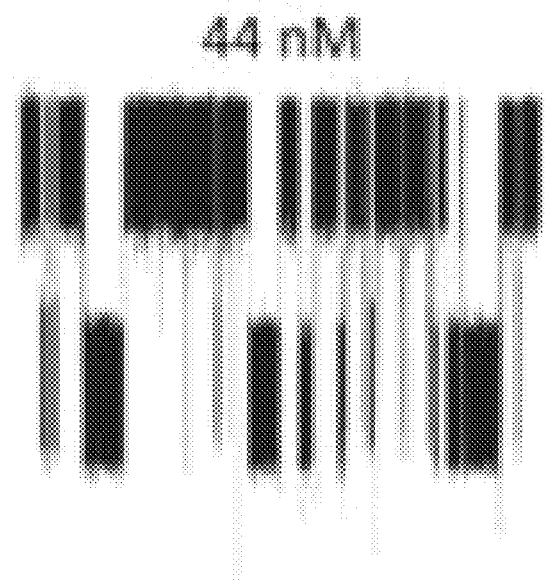
Figure 8D:
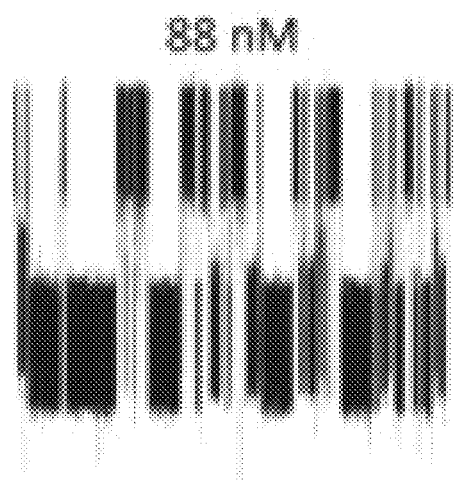
Figure 8E:
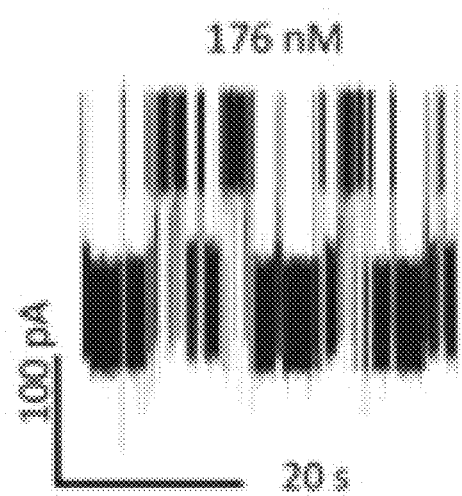
Figure 8F:
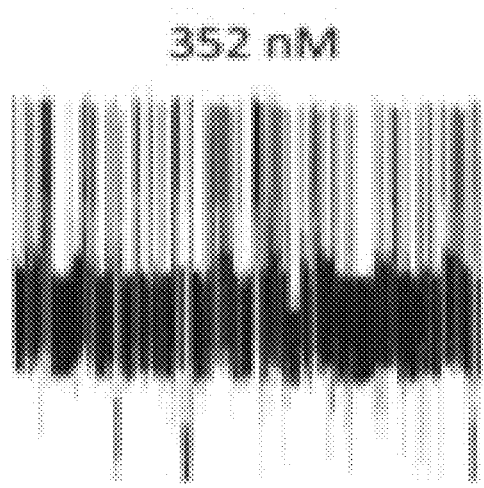
Figure 9A:
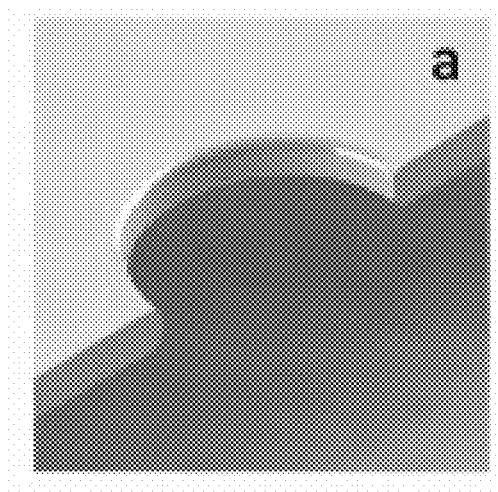
FIG. 9A depicts a schematic of a lipid bilayer and expected annulus shape of a cylindrical aperture, in accordance with an embodiment of the invention.
Figure 9B:
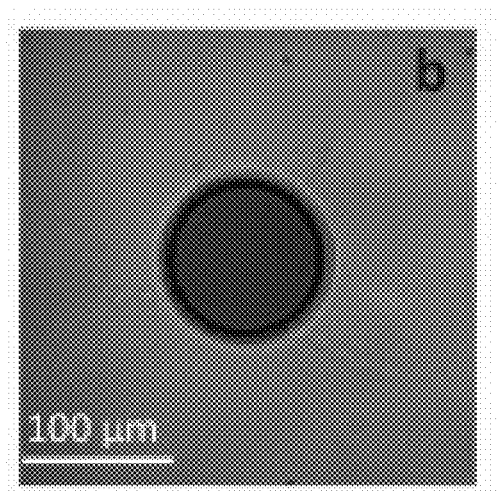
FIG. 9B depicts a microscope image of a lipid bilayer and expected annulus shape of a cylindrical aperture, in accordance with an embodiment of the invention.
Figure 9C:
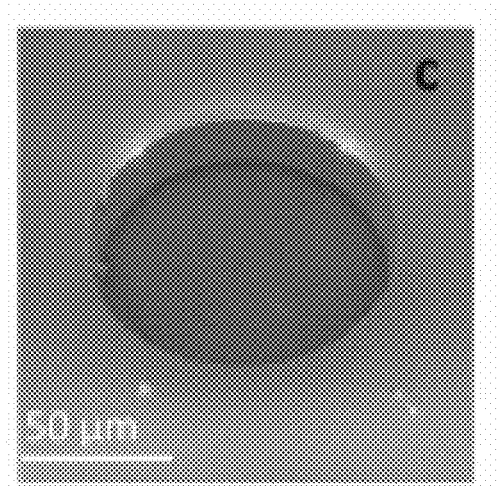
FIG. 9C depicts a scanning electron microscope image of a lipid bilayer and expected annulus shape of a cylindrical aperture, in accordance with an embodiment of the invention.
Figure 9D:
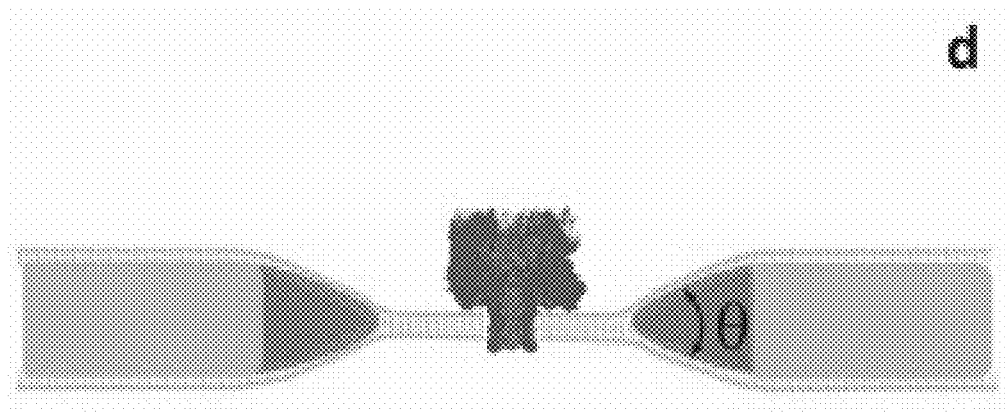
FIG. 9D depicts a diagram of a structure of a lipid bilayer and expected annulus shape of a cylindrical aperture, in accordance with an embodiment of the invention.
Figure 9E:
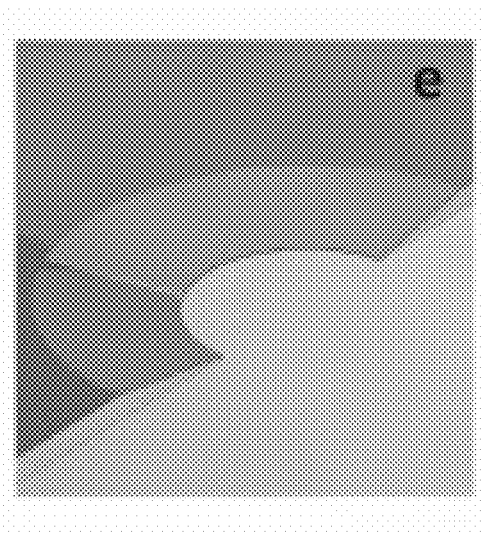
FIG. 9E depicts a schematic of a lipid bilayer and expected annulus shape of a wedge-shaped aperture, in accordance with an embodiment of the invention.
Figure 9F:
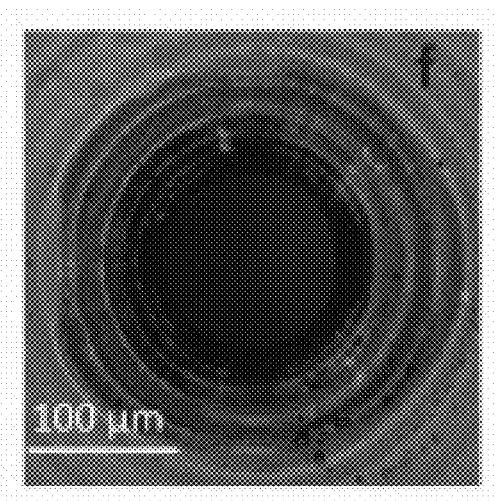
FIG. 9F depicts a microscopic image of a lipid bilayer and expected annulus shape of a wedge-shaped aperture, in accordance with an embodiment of the invention.
Figure 9G:
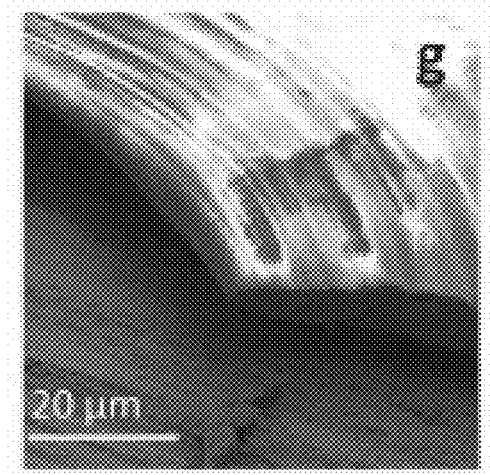
FIG. 9G depicts a scanning electron microscope image of a lipid bilayer and expected annulus shape of a wedge-shaped aperture, in accordance with an embodiment of the invention.
Figure 9H:
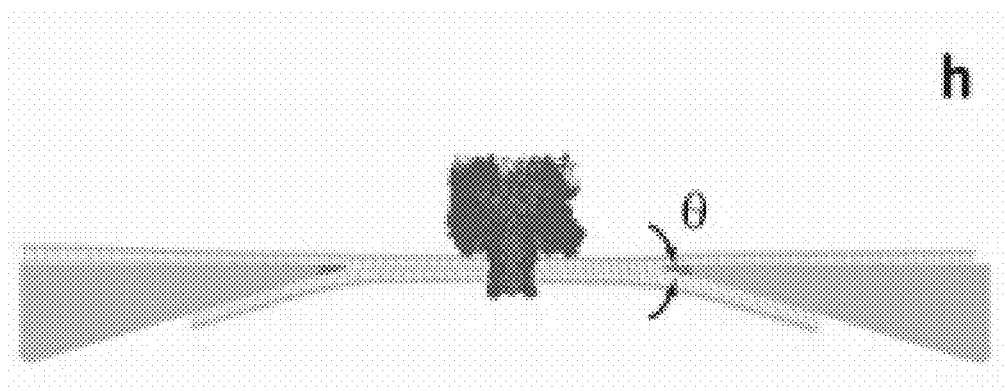
FIG. 9H depicts a diagram of a structure of a lipid bilayer and expected annulus shape of a wedge-shaped aperture, in accordance with an embodiment of the invention.

The fact that three data populations associate with the three hairpins, which can be unambiguously differentiated, implies that multiple bits of data (3 bits here) can be chemically stored in a small droplet and read using a nanopore. Moreover, each bit can get a value corresponding to the concentration of the molecule. In the other word, the number of values that can be attributed to a bit is determined by resolution of the nanopore in converting the detectable concentration range to digitized values. Consequently, $N^m$ states can be attributed to a droplet of hairpin mixture, with m being the number of species (3 here) and N the number of differentiable concentrations. FIG. 8B demonstrates the differentiation of six different concentrations based on their capture rates. Nonetheless, α-hemolysin nanopores are capable of resolving many more bins, and additionally the upper limit of concentration can be further increased. Also, 3 bp hairpins can be used for the sake of data storage as it produces a distinct current blockade level similar to longer hairpins. This increases the number of bits to 4 (m=4). Assuming that 20 discrete values of concentration for each of the 4 hairpins can be read with a nanopore, each droplet can store a value between 0 to $20^4-1$, which is equivalent of a 17-digit binary number. An important aspect of storing data in the hairpins is the fact that data can be easily encrypted in long biotinylated hairpins and decrypted using a unique restriction enzyme, as demonstrated in FIG. 4C. It is worthwhile mentioning that in this study, the 3 bp hairpins were not considered for the sake of biosensing, as they pose challenges for sensing at high applied voltage biases due to their short translocation time scales. Additionally, proximity of the restriction site to the hairpin loop significantly reduces the enzyme activity for these hairpins.

While example embodiments have been particularly shown and described, it will be understood by those skilled in the art that various changes in form and details may be made therein without departing from the scope of the embodiments disclosed hereinabove and below.

What is claimed is:

1. An apparatus for sensing a molecule, the apparatus comprising:
    a housing defining a volume;
    a divider element in the housing that defines a first chamber and a second chamber within the volume, the divider element further defining a gap for fluidic communication between the first and second chambers, the divider element decreasing in thickness from a distal location to a proximal location relative to the gap, the first and second chambers capable of containing a sample with a molecule therein;
    multiple structural elements extending from a surface of the divider element between the distal location and proximal location within the second chamber, wherein adjacent structural elements are separated by a respective distance;
    a chemical layer coupled to the divider element on opposing surfaces of the divider element, the chemical layer forming an aperture in the gap of sufficient dimensions for a given molecule to pass therethrough;
    a first electrode disposed within the first chamber and a second electrode disposed within the second chamber, the first and second electrodes composing an electrode pair that, when energized, generates an electric field at a level sufficient to cause the molecule to pass from the first chamber via the aperture to the second chamber; and
    a sensor configured to sense the molecule as it passes through the aperture.

2. The apparatus of claim 1, wherein the multiple structural elements have a geometric shape with size varying from the distal location to the proximal location and wherein the adjacent structural elements vary in respective distance from the distal location to the proximal location.

3. The apparatus of claim 2, wherein the multiple structural elements are cylindrical pillars.

4. The apparatus of claim 2, wherein the adjacent structural elements have respective distances that facilitate a capillary action of a fluid at the proximal location relative to the distal location among the multiple structural elements.

5. The apparatus of claim 1, wherein the multiple structural elements have a height extending from a surface of the divider element approximately to a common plane offset from the surface of the divider element.

6. The apparatus of claim 1, wherein the gap is substantially circular and has a diameter from about 50 μm to about 250 μm.

7. The apparatus of claim 1, wherein the aperture has a dimension that facilitates the passage of the molecule therethrough in a manner that denatures the molecule.

8. The apparatus of claim 1, wherein the chemical layer is configured to withstand a voltage differential from about 100 mV to about 400 mV at the aperture for up to eight hours.

9. The apparatus of claim 1, wherein the sensor has a sensitivity to detect or measure a voltage or current change provided to the first electrode or the second electrode during passage of the molecule through the aperture.

10. The apparatus of claim 1, wherein the sensor is electronic and has a sensitivity that enables the sensor to detect or measure a change in voltage or current provided to the first electrode or the second electrode during passage of a hairpin molecule through the aperture.

11. The apparatus of claim 10, wherein the sensor has sufficient sensitivity to discriminate between different hairpin molecules, the different hairpin molecules having a distinguishing feature.

12. The apparatus of claim 11, wherein the distinguishing feature includes a number of base pairs or a sequence mismatch.

13. The apparatus of claim 1, further comprising a power source electrically coupled to the first electrode and the second electrode.

* * * * *